(12) United States Patent
Kobayashi et al.

(10) Patent No.: US 9,233,017 B2
(45) Date of Patent: Jan. 12, 2016

(54) LOWER BACK ASSISTANCE APPARATUS

(75) Inventors: Hiroshi Kobayashi, Chiba (JP); Takuya Hashimoto, Tokyo (JP); Yutaka Sato, Chiba (JP); Eiji Ishowata, Chiba (JP); Keita Suzuki, Tokyo (JP); Hiroyuki Kobayashi, Saitama (JP); Kouhei Yamamoto, Inbaraki (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 786 days.

(21) Appl. No.: 13/498,286

(22) PCT Filed: Mar. 4, 2010

(86) PCT No.: PCT/JP2010/053567
§ 371 (c)(1),
(2), (4) Date: Mar. 26, 2012

(87) PCT Pub. No.: WO2011/036906
PCT Pub. Date: Mar. 31, 2011

(65) Prior Publication Data
US 2012/0184881 A1    Jul. 19, 2012

(30) Foreign Application Priority Data

Sep. 28, 2009   (JP) ................................ 2009-222636

(51) Int. Cl.
*A61H 1/02*    (2006.01)
*A61F 5/01*    (2006.01)
*A61F 5/02*    (2006.01)

(52) U.S. Cl.
CPC . *A61F 5/01* (2013.01); *A61F 5/026* (2013.01); *A61F 2005/0169* (2013.01); *A61F 2005/0179* (2013.01)

(58) Field of Classification Search
USPC .......... 601/5, 23, 33, 34, 35, 84, 97, 98, 105; 602/5, 16, 19, 23; 128/845
See application file for complete search history.

(56) References Cited

U.S. PATENT DOCUMENTS

2005/0130815 A1*   6/2005   Abdoli-Eramaki ........... 482/121
2008/0161738 A1    7/2008   Giesen
(Continued)

FOREIGN PATENT DOCUMENTS

DE      102004008509 A1    11/2004
FR           2864891 A1     7/2005
(Continued)

OTHER PUBLICATIONS

Notification of the First Office Action for Chinese Application No. 201080042916.3, dated Aug. 21, 2013.
(Continued)

*Primary Examiner* — Quang D Thanh
(74) *Attorney, Agent, or Firm* — Marshall, Gerstein & Borun LLP

(57) ABSTRACT

A lower back assistance apparatus including: a back frame 14 mounted to the back of a user and capable of movement following a user tilting forward; shoulder straps 22 that are attached to a back mounting section and extend towards the user trunk forward side for supporting the trunk of a user from the forward side; thigh plates 18 for mounting to the front of lower limbs of the user; coupling frames 20 with one end coupled to the thigh plates 18 and the other end coupled to the back frame 14 by joint sections 16 so as to allow relative movement with respect to the back frame 14, and capable of maintaining a non-bent profile during the relative movement; and actuators 40 that in an actuated state prevent the back frame 14 from tilting in the user forward direction.

7 Claims, 27 Drawing Sheets

(56) References Cited

U.S. PATENT DOCUMENTS

| | | | |
|---|---|---|---|
| 2011/0264014 A1* | 10/2011 | Angold | 601/35 |
| 2013/0131560 A1* | 5/2013 | Ferguson et al. | 601/33 |
| 2013/0184626 A1* | 7/2013 | Kazerooni et al. | 602/19 |
| 2014/0121573 A1* | 5/2014 | Kazerooni et al. | 601/23 |

FOREIGN PATENT DOCUMENTS

| | | |
|---|---|---|
| JP | 2736619 B2 | 4/1998 |
| JP | 2000051289 | 2/2000 |
| JP | 2003265548 | 9/2003 |
| JP | 200911818 | 1/2009 |

OTHER PUBLICATIONS

Search Report in EP Application No. 10818583.6 dated Mar. 20, 2014.

International Search Report for PCT/JP2010/053567 dated Apr. 20, 2010.

* cited by examiner

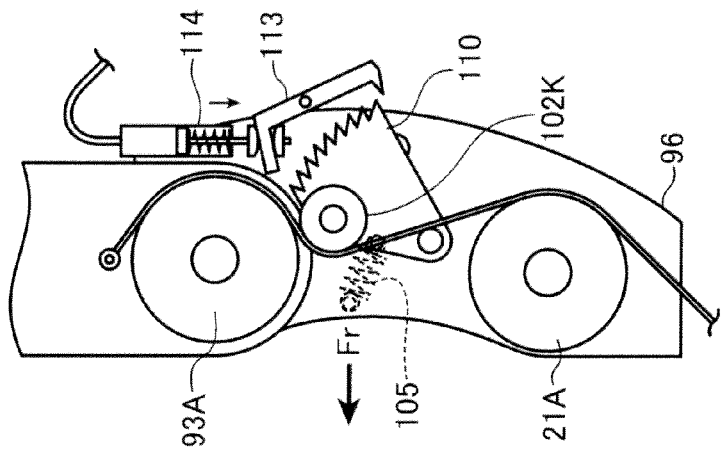
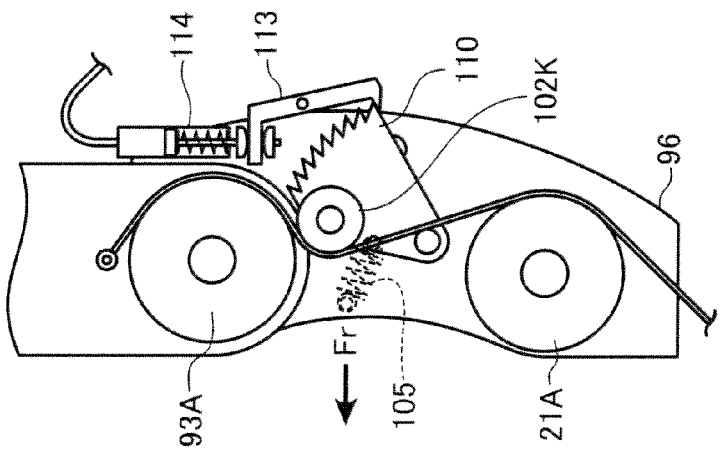
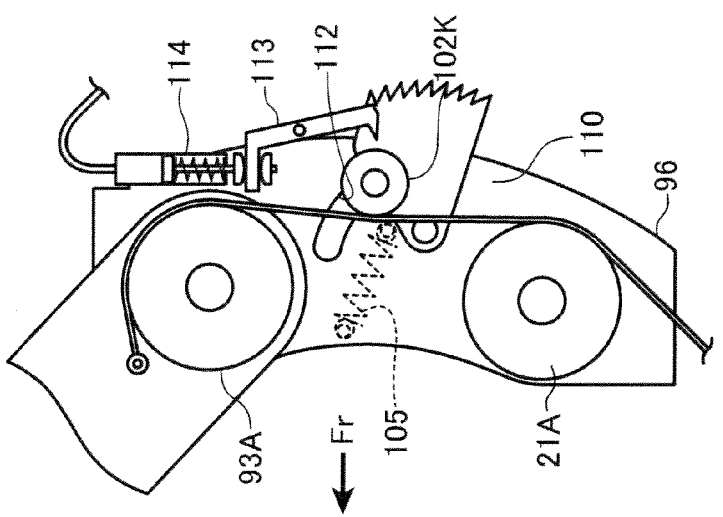

LOWER BACK ASSISTANCE APPARATUS

TECHNICAL FIELD

The present invention relates to a lower back assistance apparatus.

BACKGROUND ART

Assistance apparatuses are known for assisting forward bending action of the upper body of a user. For example, in Japanese Patent Laid-Open No. 2009-011818, a lower back assistance apparatus is disclosed that is provided with a lumbar mounting section and a back mounting section, a joint section that connects the back mounting section to the lumbar mounting section to enable the user to tilt forward, and a first actuator to control the tilting of the back mounting section in the user forward direction in an operating state.

The lower back assistance apparatus of JP-A No. 2009-011818 is also provided with a lower limb mounting section mounted to the lower limbs of the user and a tight binding member to tightly connect the lower limb mounting section to the lumbar mounting section, restricting rotation of the lumbar mounting section in the same direction as the back mounting section. Due to the tight binding member being configured from an easily deforming material such as rubber tubing, there are occasions when looseness occurs in the tight binding member depending on the posture of the user, such that the position of the lower limb mounting section slips. When the first actuator is actuated with the tight binding member still in a loose state and the lower limb mounting section still in a slipped position. the displacement of the first actuator is sometimes spent correcting the looseness of the tight binding member and the slipped position of the lower limb mounting section, such that raising force is not appropriately transmitted to the back mounting section.

DISCLOSURE OF INVENTION

Technical Problem

In consideration of the above circumstances, an object of the present invention is to provide a lower back assistance apparatus that is able to stabilize and assist forward bending actions of a user mounted with the lower back assistance apparatus.

Solution to Problem

A lower back assistance apparatus of a first aspect includes: an upper body mounting section for mounting to an upper body of a user and capable of following movement of a user tilting forward; a support section attached to the upper body mounting section, extending towards a user trunk front side or trunk rear side, and supporting the user at the trunk front side or trunk rear side; a lower limb mounting section for mounting to a lower limb of the user at least at the front side of the lower limb; a coupling section a portion at a first end of the coupling section being coupled to the lower limb mounting section. a portion at the second end of the coupling section being coupled by a joint section so as to enable relative movement of the coupling section with respect to the upper body mounting section so as to permit the following movement of the upper body mounting section, and the coupling section being capable of maintaining a non-bent profile during the relative movement; and an actuator that in an actuated state causes a force to act on the upper body mounting section countering the forward tilting of the user.

In a lower back assistance apparatus of the first aspect. the upper body mounting section is mounted to the upper body of the user (either at the back or at the chest)so as to allow following movement of the user tilting forward. The support section is attached to the upper body mounting section, extends towards a user trunk front side or trunk rear side, and supports the user at the trunk front side or trunk rear side. The lower limb mounting section is mounted to at least the front side of a lower limb of the user.

The coupling section is coupled to the lower limb mounting section at a portion at a first end, and is coupled by a joint section at a portion at the second end so as to allow relative movement of the coupling section with respect to the upper body mounting section. Coupling to the upper body mounting section is performed such as to permit the following movement of the upper body mounting section. The coupling section is also configured such that it is capable of maintaining a non-bent profile during the relative movement.

When a user performs a forward bending action, the upper body mounting section moves to following tilting in the user forward direction. When the actuator is actuated in the bent-forward state, a force acts on the upper body mounting section countering tilting of the user forward. As the coupling section that is coupled to the lower limb mounting section is capable of maintaining a non-bent profile, force acts on the upper body mounting section in the opposite direction, and force acts in a direction to cause relative movement between the upper body mounting section and the coupling section. The reaction force of the coupling section can be employed to stabilize and apply force to the back mounting section due to the second end of the coupling section being maintained at a specific position by the lower limb mounting section.

The effort required by a user when in a forward tilting posture is reduced due to the force countering the forwards tilt when a user entrusts their upper body weight to the support section fitted to the upper body mounting section or rests against the upper body mounting section.

In a lower back assistance apparatus of a second aspect, the actuator operates to cause a force to act on the upper body mounting section in a user raising direction.

It is therefore possible to provide assistance to a user raising action as well as to reduce the effort required by a user when in a forward tilting posture due to the actuator causing force to act on the upper body mounting section in the user raising direction.

In a lower back assistance apparatus of a third aspect the joint section is configured to enable relative rotation between the upper body mounting section and the coupling section about an axis running along a user left-right direction.

In the lower back assistance apparatus of the third aspect, during a forward bending action by the user, the upper body mounting section and the coupling section rotate relative to each other about an axis running along the user left-right direction. Tilting of the back mounting section in the forwards direction is stopped when the actuator is actuated, due to force being applied to the upper body mounting section and the coupling section in the direction to cause relative rotation in the opposite direction to the direction when bending forward.

In a lower back assistance apparatus of a fourth aspect the coupling section further includes a second joint section further to a lower limb mounting section side than the first joint section, and the second joint section enables relative rotation between the lower limb mounting section and the coupling section about an axis running along the user left-right direction.

In a lower back assistance apparatus of a fourth aspect, during a forward bending action by the user, it is possible to achieve a shape more closely following the bent-forward state of the user, from the upper body mounting section via the coupling section through to the lower limb mounting section, due to relative rotation being possible between the lower limb mounting section and the coupling section at the second joint section about an axis running along the user left-right direction.

In a lower back assistance apparatus of a fifth aspect, configuration is made such that relative rotation is possible between the upper body mounting section and the coupling section about an axis running along a user front-rear direction.

According to a lower back assistance apparatus of a fifth aspect, it is possible to raise the degrees of freedom of lower limb action of the user due to the coupling section being able to rotate with respect to the upper body mounting section in the direction moving away from the trunk.

In a lower back assistance apparatus of a sixth aspect, the coupling section and the upper body mounting section are coupled together by the joint section, and the lower back assistance apparatus further includes a lumbar mounting section for mounting to a lumbar region of the user.

According to a lower back assistance apparatus of a sixth aspect, assistance to a forward tilting posture can be performed more stably due to the upper body mounting section being prevented by the lumbar mounting section from moving in the user forward direction when the actuator is actuated.

A lower back assistance apparatus of a seventh aspect further includes a buttock mounting section coupled to the coupling section and mounted to the buttocks of the user.

According to a lower back assistance apparatus of a seventh aspect, assistance can be performed more stably to a forward tilting posture, due to the upper body mounting section being prevented by the buttock mounting section from moving in the user forward direction when the actuator is actuated.

In a lower back assistance apparatus of an eighth aspect, the actuator is a pneumatic actuator that contracts when internally supplied with air.

Tilting of the upper body mounting section in the user forward direction can accordingly be stopped by employing the pneumatic actuator as the actuator.

Note that, as according to a ninth aspect, the actuator of the present invention may be disposed at the upper body mounting section, disposed to the coupling section, or disposed to both of these sections.

In a lower back assistance apparatus of a tenth aspect: a wire extends out from a first end of the actuator; and a clutch mechanism is provided at the joint section, the clutch mechanism is provided with a rotation body with a peripheral section around which the wire is wrapped, and the clutch mechanism is configured so as to fix the rotation body to the upper body mounting section or to the coupling section when the actuator is actuated such that tension force of the wire acts on the upper body mounting section or on the coupling section from the time of initial actuation of the actuator.

In a lower back assistance apparatus of the tenth aspect, a wire extending out from a first end of the actuator is wrapped around a peripheral section of the rotation body. Due to the positional relationship of the upper body mounting section and the coupling section changing with their relative movement, the length of the wire, including the wrapped portion, is made to correspond to the relative movement. When the actuator is actuated it is possible for the tension force of the wire to act on the upper body mounting section or the coupling section from the time of initial actuation of the actuator, regardless of the length of the wire, due to the rotation body being fixed to the upper body mounting section or to the coupling section.

In a lower back assistance apparatus of eleventh aspect: a wire extends out from a first end of the actuator; and a pretension application mechanism is provided at the joint section, the pretension application mechanism is provided with a rotation body with a peripheral section around which the wire is wrapped, and the pretension application mechanism applies pretension to the wire such that tension force of the wire acts on the upper body mounting section or on the coupling section from the time of initial actuation of the actuator.

In a lower back assistance apparatus of the eleventh aspect, the wire extending out from a first end of the actuator is wrapped around the peripheral section of the rotation body. Due to the positional relationship of the upper body mounting section and the coupling section changing with their relative movement, the length of the wire, including the wrapped portion, is made to correspond to the relative movement. It is therefore possible for the tension force of the wire to act on the upper body mounting section or the coupling section from the time of initial actuation of the actuator due to pretension having been applied by the pretension application mechanism. a clutch mechanism is provided at the first joint section, the clutch mechanism is provided with a block section with a peripheral section around which the wire is wrapped, and the clutch mechanism is configured so as to press the block section toward the user forward direction against the wire Advantageous Effects of Invention According to the present invention as described above, the forward tilting posture of a user can be stabilized and assisted when mounted with the lower back assistance apparatus.

BRIEF DESCRIPTION OF DRAWINGS

FIG. 27A is an expanded drawing of the vicinity of an upper coupling frame 96 according to a modified example of the third exemplary embodiment of the present invention.

FIG. 27B is an expanded drawing of the vicinity of the upper coupling frame 96 according to a modified example of the third exemplary embodiment of the present invention.

FIG. 27C is an expanded drawing of the vicinity of the upper coupling frame 96 according to a modified example of the third exemplary embodiment of the present invention.

BEST MODE FOR CARRYING OUT THE INVENTION

First Exemplary Embodiment

Figure 1:
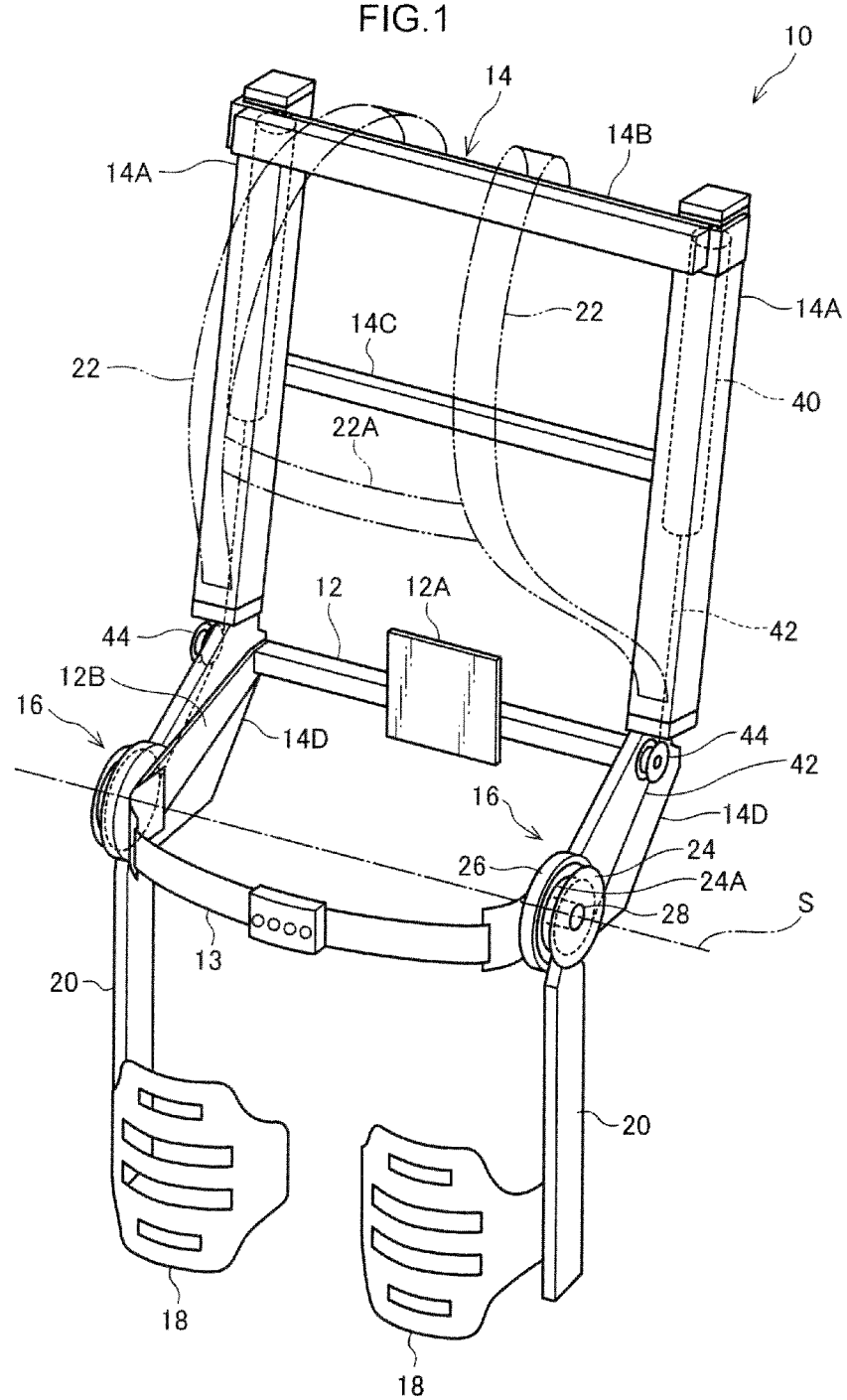
FIG. 1 is a perspective view illustrating a lower back assistance apparatus according to a first exemplary embodiment of the present invention.

Detailed explanation follows regarding a first exemplary embodiment of the present invention, with reference to the drawings. For ease of explanation the front side is taken as the arrow FR direction in the drawings, indicating the front direction side for a user, and up, down, left and right are directions based on facing towards the front side direction.

Figure 2:
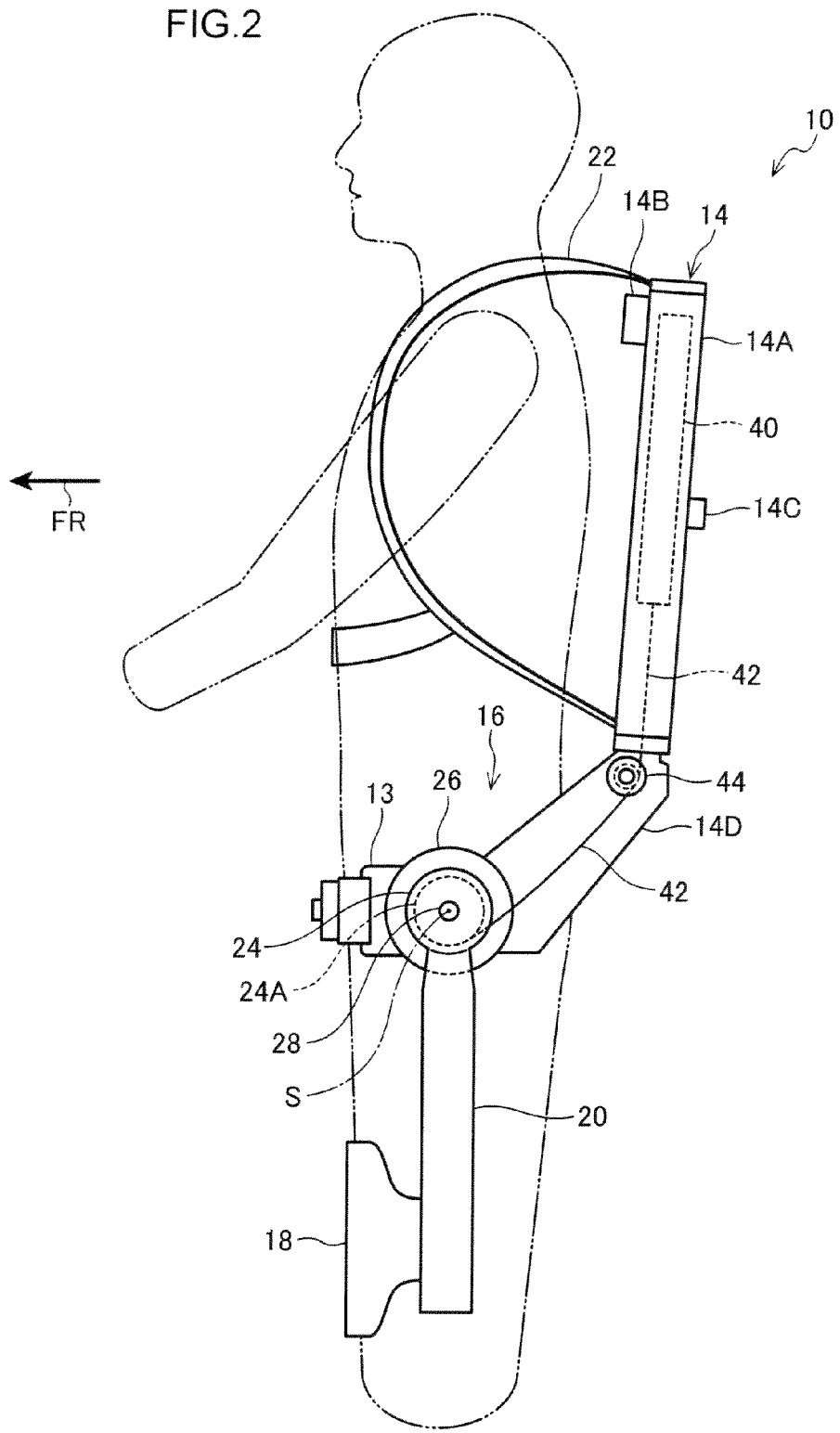
FIG. 2 is a side view illustrating a state of use of a lower back assistance apparatus according to the first exemplary embodiment of the present invention.
Figure 3:
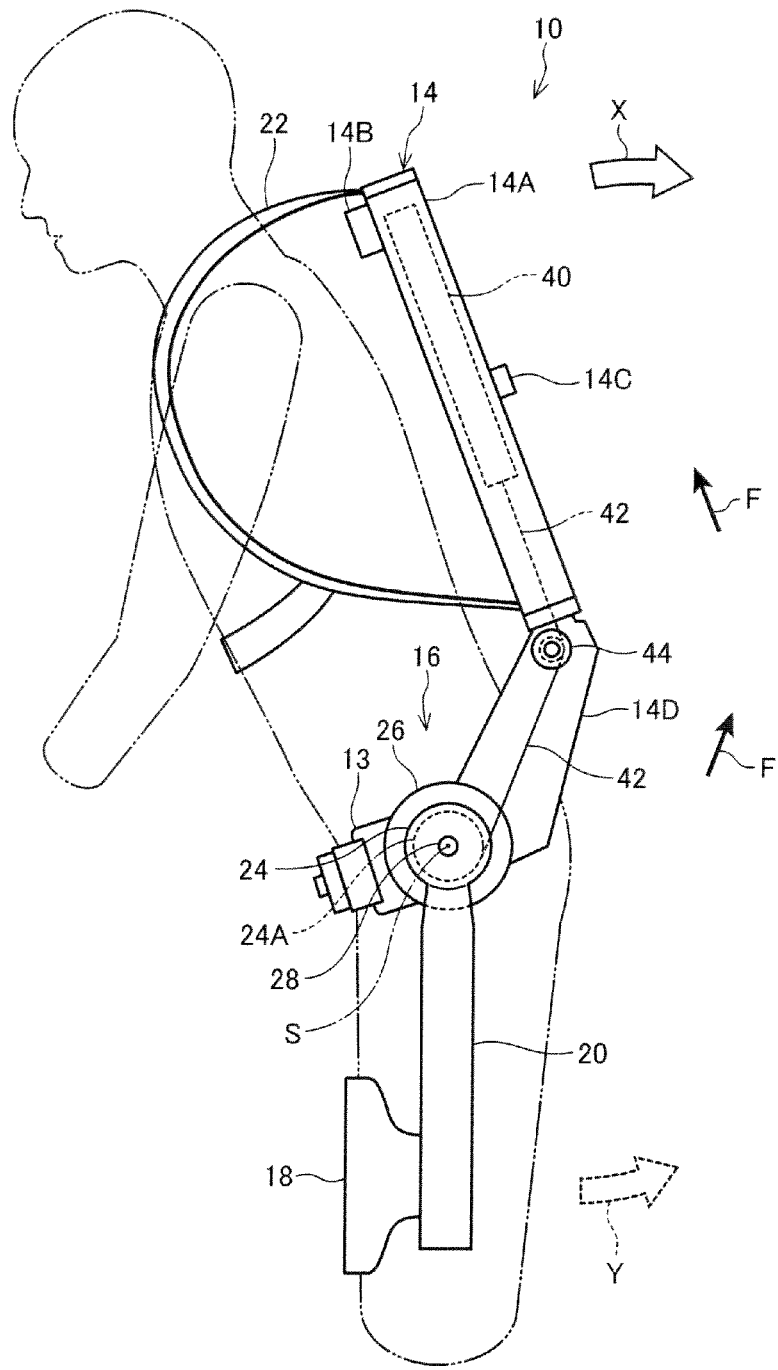
FIG. 3 is a side view illustrating a state of use of a lower back assistance apparatus according to the first exemplary embodiment of the present invention.

A lower back assistance apparatus 10 according to the first exemplary embodiment is illustrated in FIG. 1 to FIG. 3. FIG. 1 illustrates the lower back assistance apparatus 10 in a pre-mounted state, and FIG. 2 and FIG. 3 illustrate the lower back assistance apparatus 10 in a state mounted to a user. As shown in these drawings, the lower back assistance apparatus 10 includes a back frame 14 serving as an upper body mounting section, shoulder straps 22 serving as front support sections, thigh plates 18 serving as lower limb mounting sections and coupling frames 20 serving as coupling sections.

The back frame 14 is mounted to the back of a user and includes a left and right pair of side frame sections 14A. and center frame sections 14B, 14C for coupling together the left and right pair of side frame sections 14A. The left and right pair of side frame sections 14A is configured so as to be left-right symmetrical to each other.

The side frame sections 14A are formed by elongated tubes, and are disposed separated from each other aligned along the top-bottom direction of the back of a user. Lower side sections 14D are coupled and fixed to the bottom ends of the side frame sections 14A. The lower side sections 14D extend diagonally forwards out from the bottom ends of each of the left and right pair of side frame sections 14A, and are disposed at both the left and right edges of the lumbar region of a user.

The center frame section 14B is disposed so as to be connected to the top ends of the left and right pair of side frame sections 14A, and the center frame section 14C is disposed so as to be connected to an intermediate portion on each of the left and right pair of side frame sections 14A.

A lumbar frame section 12 serving us a lumbar mounting section is provided to the lower side sections 14D. The lumbar frame section 12 is disposed substantially parallel to the center frame section 14B so as to span across between the left and right pair of lower side sections 14D. A lumbar plate 12A is attached at the center of the lumbar frame section 12. The back frame 14 and the coupling frames 20 are coupled together by joint sections 16 provided at both the leading ends of the C-shaped lumbar frame section 12, such that the back frame 14 and the coupling frames 20 are able to rotate relative to each other.

A block 44 is configured at the upper end of each of the lower side sections 14D. A wire 42, described later, is wrapped around each of the blocks 44, and the blocks 44 guide the direction of the wires 42 from the back face side of a user out diagonally forwards.

The shoulder straps 22 are attached to the side frame sections 14A. The shoulder straps 22 are provided in a left and right pair, and one end of each of the shoulder straps 22 is attached towards the center of the center frame section 14B, and the other end of the shoulder straps 22 is attached to the lower end portion of the respective side frame section 14A. The left and right pair of shoulder straps 22 are each linked together by a belt 22A at central portions of the shoulder straps 22. The shoulder straps 22 are tightly fitted to the upper body of a user such that the back frame 14 does not slip.

The joint sections 16 are configured at the lower ends of the lower side sections 14D. The coupling frames 20 and the back frame 14 (the lower side sections 14D) are coupled together by the joint sections 16. A waist belt 13 is provided to the fronts of the joint sections 16. The waist belt 13 is disposed in front of the waist of a user, spanning across between the left and right pair of joint sections 16 so as to couple together the joint sections 16. Further details regarding the joint sections 16 are described later.

The coupling frames 20 are formed in an elongated shape and are disposed along the lower limbs of the user. One end (the top end) of each of the coupling frames 20 is coupled to the lower side section 14D using the joint section 16. The lower side sections 14D and the coupling frames 20 are coupled together so as to be rotatable relative to each other about a rotation axis S disposed along the user left-right direction. The coupling frames 20 are configured by rigid members that do not bend even when rotated relative to the back frame 14.

Thigh plates 18 are fixed to the side of the coupling frames 20 at the other end. The thigh plates 18 are formed in a curved shape to cover the front of the lower limbs of a user. The thigh plates 18 are disposed at the front of the lower limbs of a user.

Each of the joint sections 16 includes a plate 26 fixed to a portion at the lower end of the lower side section 14D, a rotation shaft 28 that projects out from the plate 26 towards the shoulder width direction outside, and a circular plate shaped rotation body 24 that is rotatably supported on the rotation shaft 28. End portions 12B are disposed at the two ends of the lumbar frame section 12. The left and right pair of joint sections 16 are configured so as to be left-right symmetrical to each other.

The plates 26 are positioned at the sides of the lumbar region of a user, and the rotation shafts 28 extend out in a direction from the sides of the user lumbar region towards the shoulder width direction outside. A circular hole (not shown in the drawings) is formed at the axial center of the rotation bodies 24 for the rotation shafts 28 to fit into and allow relative rotation. Grooves 24A are formed in the peripheral faces of the rotation bodies 24 to enable the wires 42 to be wrapped around, as described later. It is not essential for the rotation bodies 24 to have a circular shape, and configuration may be made with a semi-circular plate shape or an elliptical plate shape.

The two end portions 12B of the lumbar frame section 12 are disposed at the inside of the plates 26. The two end portions 12B are attached so as to be capable of rotating about the rotation shafts 28.

One end of each of the coupling frames 20 is fixed to the respective rotation body 24. such that the coupling frames 20 are capable of rotating together with the rotation bodies 24. When the plates 26 rotate in the anticlockwise direction with respect to rotation bodies 24 as viewed from the left hand side, the back frame 14 swings in the same direction. When the plates 26 rotate with respect to the rotation bodies 24 in the clockwise direction as viewed from the left hand side, the back frame 14 also swings in the same direction.

When this occurs, the position of the coupling frames 20 is restricted to a position along the lower limbs of a user due to the thigh plates 18 being in contact from the front with the user's lower limbs. Relative rotation between the back frame 14 and the coupling frames 20 therefore occurs about the rotation shafts 28 of the joint sections 16.

Figure 4A:
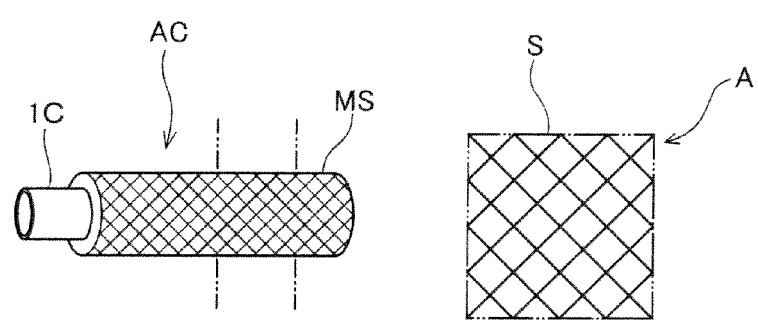
FIG. 4a is a drawing schematically showing an actuator provided to a lower back assistance apparatus according to the first exemplary embodiment of the present invention.
Figure 4B:
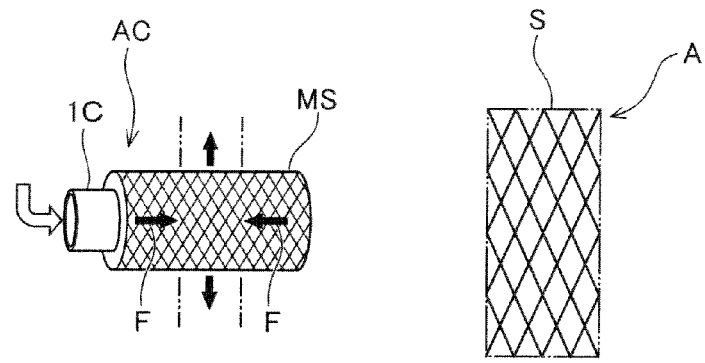
FIG. 4b is a drawing schematically showing an actuator provided to a lower back assistance apparatus according to the first exemplary embodiment of the present invention.

Actuators 40 are provided to the lower back assistance apparatus 10. The actuators 40 are housed inside the respective pair of side frame sections 14A of the back frame 14. The actuators 40 are pneumatic actuators (fluid pressure actuators, called McKibben Artificial Muscles). As illustrated in FIG. 4A and FIG. 4B, a pneumatic actuator AC includes an inner tube IC of an expandable and contractible body, and a mesh sleeve MS that is a covering body of mesh form for covering the inner tube IC. The mesh sleeve MS is for example configured from a non-extendible thread member such as a high tensile strength fiber. The two end portions in the length (axial) direction of the mesh sleeve MS are fixed to the two length direction end portions of the inner tube IC.

As shown in FIG. 4B, the inner tube IC is expanded by air being supplied into the inner tube IC. Expansion of the inner tube IC is converted by the mesh sleeve MS into a contraction in the overall length of the pneumatic actuator AC. Namely, when the air is supplied into the pneumatic actuator AC the length of the pneumatic actuator AC contracts as its diameter is expanding. Due to such contraction in length, a force F is generated towards the direction of contraction of the pneumatic actuator AC.

Figure 5:
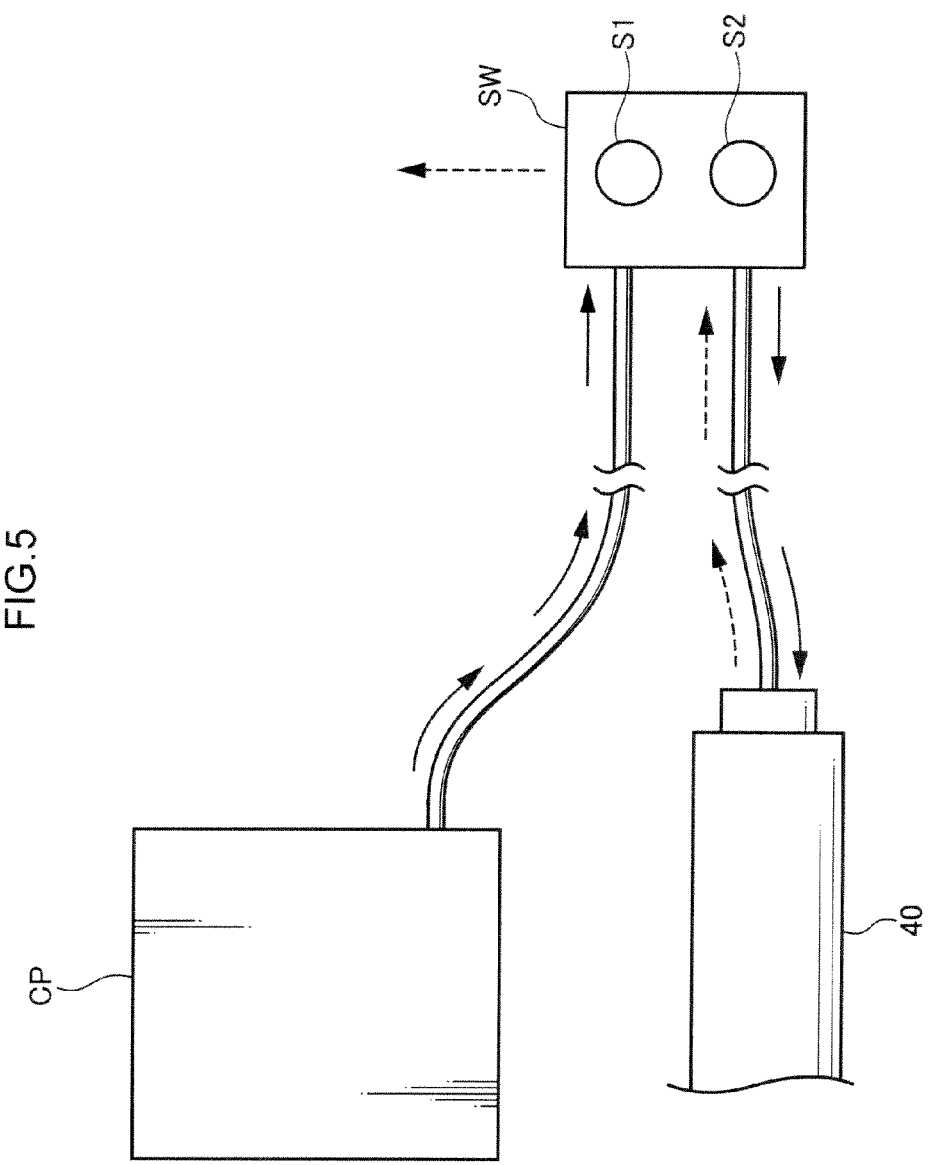
FIG. 5 is a drawing schematically showing an actuator air supply and discharge mechanism provided to a lower back assistance apparatus according to the first exemplary embodiment of the present invention.

As shown in FIG. 5, a compressor CP is connected through a switch SW to the actuators 40. The switch SW is provided with an air supply switch S1 and an air discharge switch S2. Compressed air is supplied from the compressor CP to the actuators 40 when the air supply switch S1 is switched ON and the air discharge switch S2 is switched OFF. Air inside the actuators 40 is discharged when the air discharge switch S2 is switched ON and the air supply switch S1 is switched OFF.

As shown in FIG. 1 to FIG. 3, the wire 42 is attached to the lower end side of the actuators 40. One end portion of each of the wires 42 extends out from the lower end of the actuators 40, changes direction as it is wrapped around the block 44 and is fixed in the groove 24A of the rotation body 24.

With the actuators 40 at their natural length (maximum length), the wires 42 are wrapped around the rotation bodies 24 with at least slack of the amount of increase in length when the back frame 14 tilts forward in the permissible range, namely the wires 42 are fixed to the rotation bodies 24 when the back frame 14 has been tilted forward.

Figure 6:
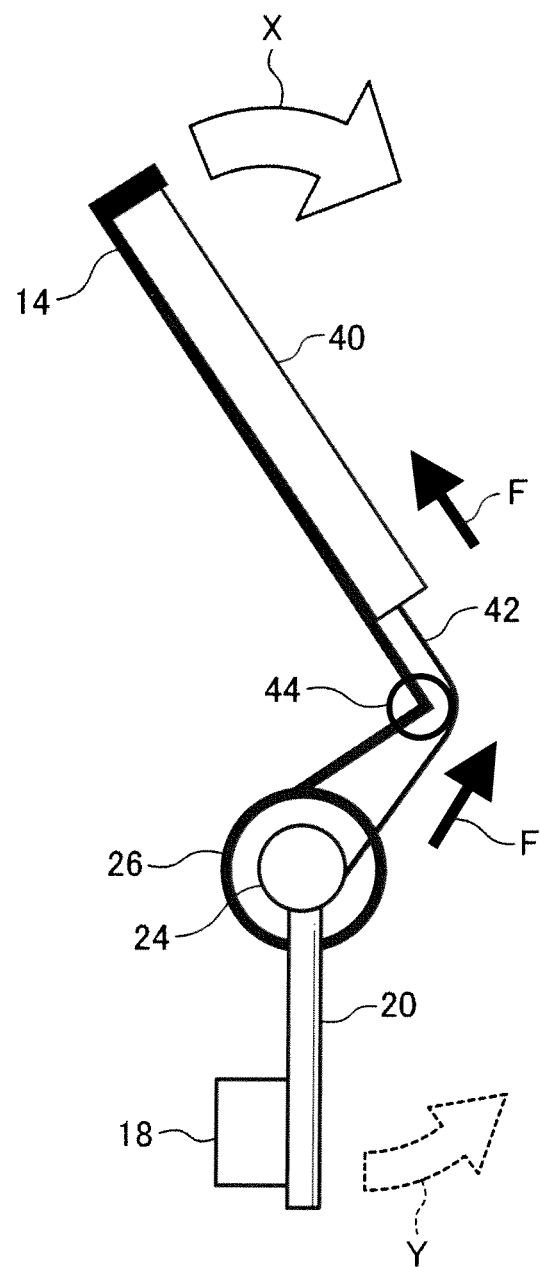
FIG. 6 is a schematic explanatory diagram of a lower back assistance apparatus according to the first exemplary embodiment of the present invention.

FIG. 6 is a simplified explanatory diagram of the lower back assistance apparatus 10 of the present exemplary embodiment. FIG. 6 illustrates a state in which the actuators 40 have been actuated with the back frame 14 in a forward tilted state.

Explanation follows regarding operation of the present exemplary embodiment.

When a user is performing a specific operation with their upper body in a forward tilted posture. such as a welding operation, if a forward bending action is performed then the back frame 14 tilts forwards to follow the forward tilting of the upper body of a user. When this occurs the back frame 14 rotates relative to the coupling frames 20 about the rotation axis S of the joint sections 16. The coupling frames 20 are restricted to a position aligned along the lower limbs of the user by the thigh plates 18.

When the air supply switch S1 of the switch SW is switched ON and the air discharge switch S2 of the switch SW is switched OFF with the back frame 14 in a forward tilted state, air supply to the actuators 40 is performed and the actuators 40 contract.

The actuators 40 contract, and partway through contraction reach a state in which there is no play left in the wires 42, with tension force F (see FIG. 3 and FIG. 6) then generated. A rotation force accordingly acts on the coupling frames 20 towards direction Y. However, the coupling frames 20 are unable to rotate in the Y direction due to being restricted by the thigh plates 18. The contraction of the actuators 40 is accordingly expressed by a rotation of the back frame 14 in the X direction. The action of a user to raise their upper body can accordingly be assisted since force acts through the shoulder straps 22 on the upper body of the forward tilted user in the raising rotation direction X. Due to force in the raising rotation direction X becoming greater than tilting force on a user towards the front, the back frame 14 is rotated towards the raising rotation direction X. and the upper body of a user can be raised.

If the air supply switch S1 of the switch SW is then switched OFF and the air discharge switch S2 of the switch SW is switched ON, air stops being supplied to the actuators 40, air pressure in the actuators 40 stops rising, and contraction of the actuators 40 stops. The rotation of the back frame 14 towards the X direction stops in this state.

When the weight of the upper body of the forward tilting user is entrusted to the shoulder straps 22 in this state (the forward tilted upper body is rested against the shoulder straps 22), the upper body adopts a state in which it hangs from the back frame 14. Consequently, the user is able to maintain the forward tilting posture without using the muscles in their lower back (such as the erector spinae). By maintaining contraction of the actuators 40 assistance to maintaining the user forward tilting posture is achieved.

Since the rotation bodies 24 are rotatable in the clockwise rotation direction as viewed from the left hand side irrespective of whether the actuators 40 are in a compressed state or not, a user is able at will to raise their upper body to an upright posture from a forward tilting posture.

According to the present exemplary embodiment, the coupling frames 20 that are formed from rigid members that have been coupled to the thigh plates 18 and maintain a non-bent state, and so the rotation force (about the rotation axis S) in the opposite direction to force on the back frame 14 can be readily made to act on the coupling frames 20 when the actuators 40 are actuated. Rotation force (reaction force) of the coupling frames 20 can accordingly be employed as a force stably acting as a force on the back frame 14 for rotation in the raising rotation direction X.

In the present exemplary embodiment the actuators 40 are each respectively disposed in the pair of side frame sections 14A, however configuration may be made in which a single actuator 40 is disposed only in one of the side frame sections 14A.

Figure 7:
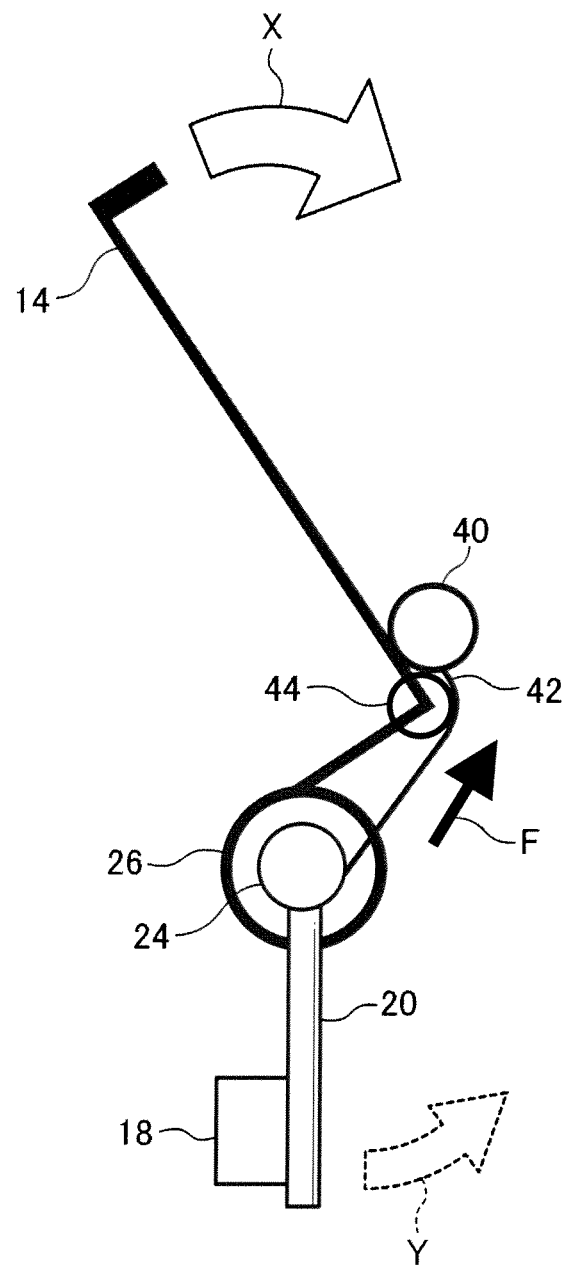
FIG. 7 is a schematic explanatory diagram of a modified example of a lower back assistance apparatus according to the first exemplary embodiment of the present invention.

The actuators 40 in the present exemplary embodiment are disposed in the up-down direction along the side frame sections 14A. However, as shown in FIG. 7, the actuators 40 may be disposed in a transverse direction along the center frame section 14C. A force can also be caused to act to rotate the back frame 14 in the raising rotation direction X in such cases, similarly to as shown in FIG. 6.

Figure 8:
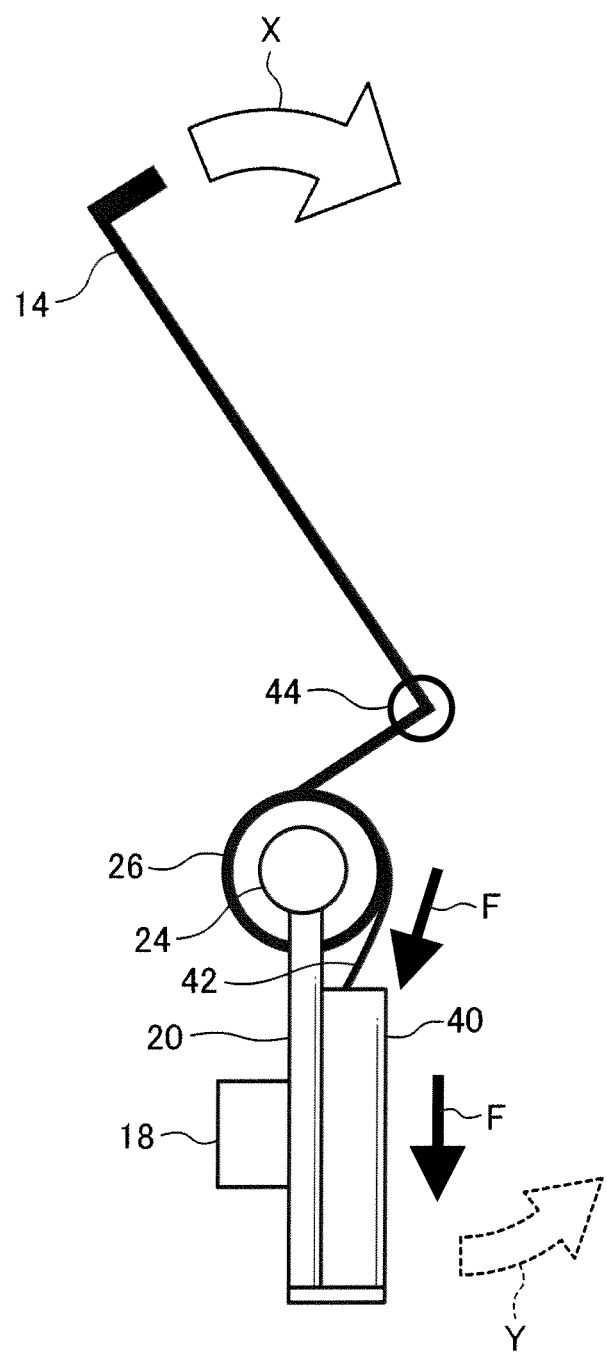
FIG. 8 is a schematic explanatory diagram of a different modified example of a lower back assistance apparatus according to the first exemplary embodiment of the present invention.

Furthermore, while explanation in the present exemplary embodiment is of an example in which the actuators 40 are mounted to the back frame 14, configuration may be made with the actuators 40 disposed on the coupling frames 20 side, as shown in FIG. 8. In such cases the wires 42 are fixed at the plate 26 side. Also in cases in which the actuators 40 are disposed at the coupling frame 20 side, force arising from the tension force F can be made to act on the back frame 14 in the raising rotation direction X, and force can be made to act on the coupling frames 20 in rotation direction Y, the opposite direction force on the back frame 14. A reduction can accordingly be achieved in the strain on a user when tilting forward, and maintaining a forward tilting posture and action to raise the upper body can be stabilized and assisted.

Figure 9:
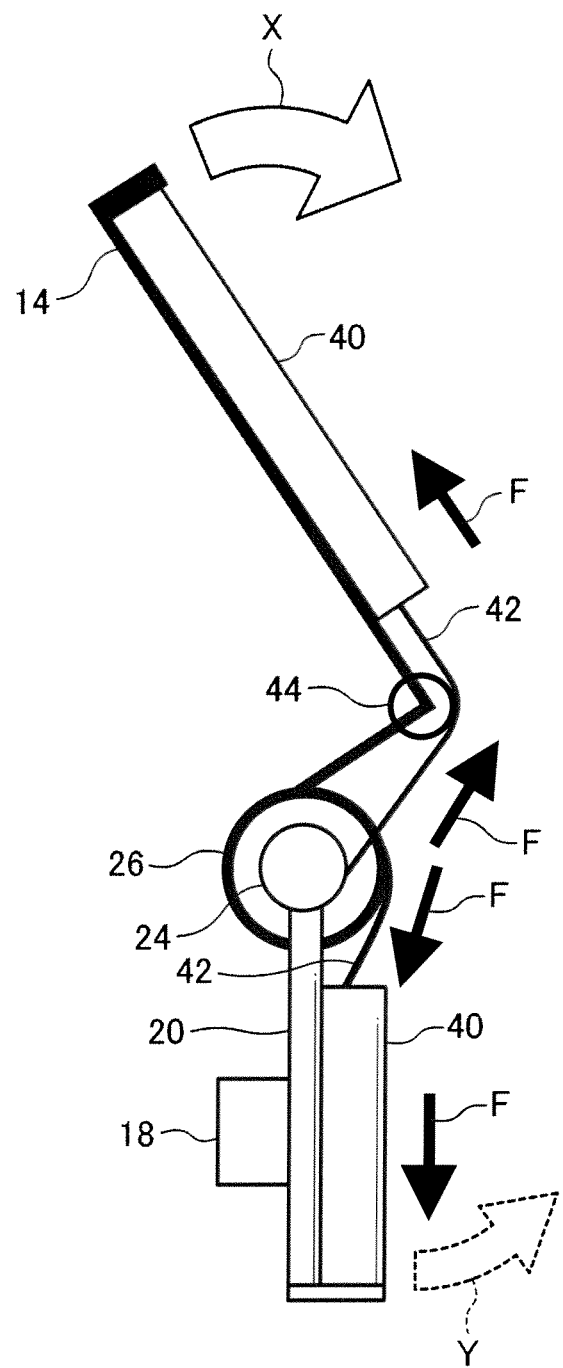
FIG. 9 is a schematic explanatory diagram of a different modified example of a lower back assistance apparatus according to the first exemplary embodiment of the present invention.

The actuators 40 may also be disposed, as shown in FIG. 9, to both the back frame 14 and the coupling frames 20.

In the present exemplary embodiment a single pneumatic actuator is employed for each single actuator 40, however configuration may be made with plural pneumatic actuators therefor depending on the assisting force required. In such cases wires 42 corresponding to the number of pneumatic actuators are fixed to the rotation bodies 24.

Figure 10A:
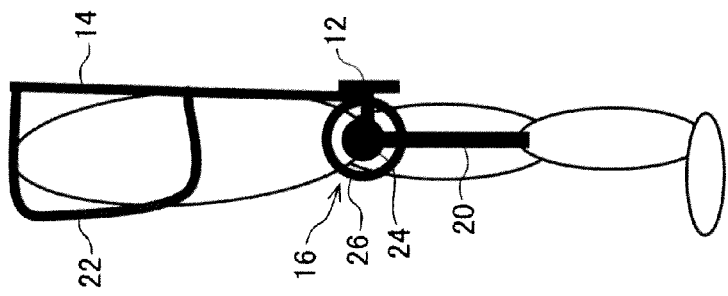
FIG. 10A is an explanatory diagram explaining the action of a lower back assistance apparatus according to the first exemplary embodiment of the present invention from which the lumbar frame section has been removed.
Figure 10B:
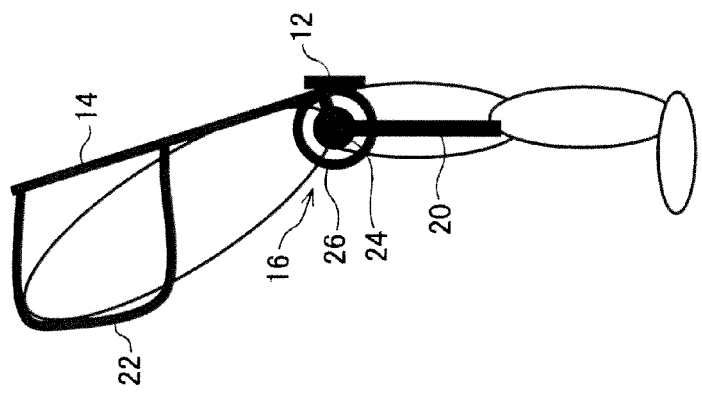
FIG. 10B is an explanatory diagram explaining the action of a lower back assistance apparatus according to the first exemplary embodiment of the present invention from which the lumbar frame section has been removed.
Figure 10C:
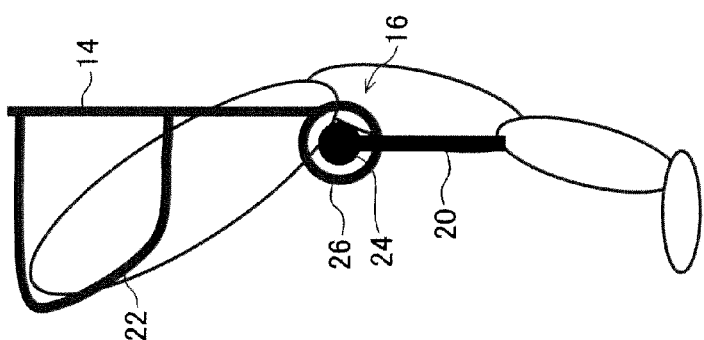
FIG. 10C is an explanatory diagram explaining the action of a lower back assistance apparatus according to the first exemplary embodiment of the present invention.
Figure 10D:
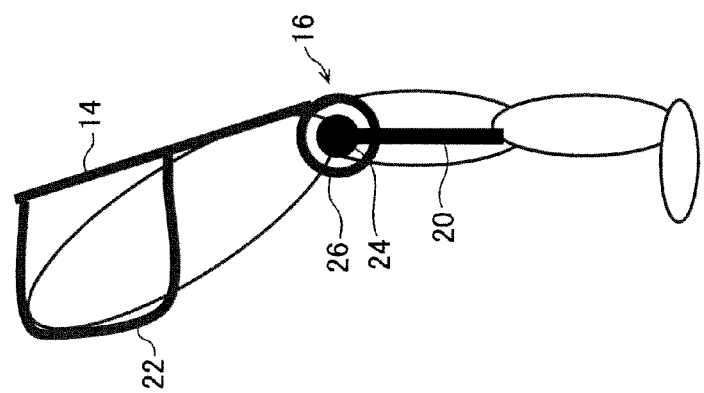
FIG. 10D is an explanatory diagram explaining the action of a lower back assistance apparatus according to the first exemplary embodiment of the present invention.

The lumbar frame section 12 is provided in the present exemplary embodiment, however the lumbar frame section 12 is not always required. In particular, movement of the back frame 14 towards the user front side when the actuators 40 are actuated can be prevented by provision of the lumbar frame section 12. Namely, in cases in which the lumbar frame section 12 is not provided, when the actuators 40 are actuated in the forward tilted state as shown in FIG. 10A, the joint sections 16 move forward as shown in FIG. 10B, rendering it difficult for the force to act in the user raising direction. However, when the lumbar frame section 12 is provided, when the actuators 40 are actuated in the forward tilted state shown in FIG. 10C, forward movement of the joint sections 16 is restricted by the lumbar frame section 12, as shown in FIG. 10D, and force can be efficiently made to act in the direction to raise a user, enabling more stable assistance to be given to a user. In place of the lumbar frame section 12, configuration may also be made with the waist belt 13 not only disposed in front of but also behind the joint sections 16, so as to fix the joint sections 16 with the waist belt to the hip joint location of the user.

In the present exemplary embodiment the thigh plates 18 are configured in a shape covering only the front side of the lower limbs of the user, however the thigh plates 18 may be configured to cover around the whole periphery of the lower limbs of the user. In particular, complicated mounting can be avoided by only covering the front, and user wearing comfort can be enhanced compared to when configuration is made covering around the whole of the periphery.

Second Exemplary Embodiment

Explanation follows regarding the second exemplary embodiment of the present invention. Parts of the configuration similar to those of the first exemplary embodiment are allocated the same reference numerals and detailed explanation thereof is omitted.

A lower back assistance apparatus 50 of the present exemplary embodiment differs from the first exemplary embodiment in that the actuators are disposed on the coupling frame 20 side. Joint sections 16 also differ from those of the first exemplary embodiment in that they are provided with a clutch mechanism.

Figure 11:
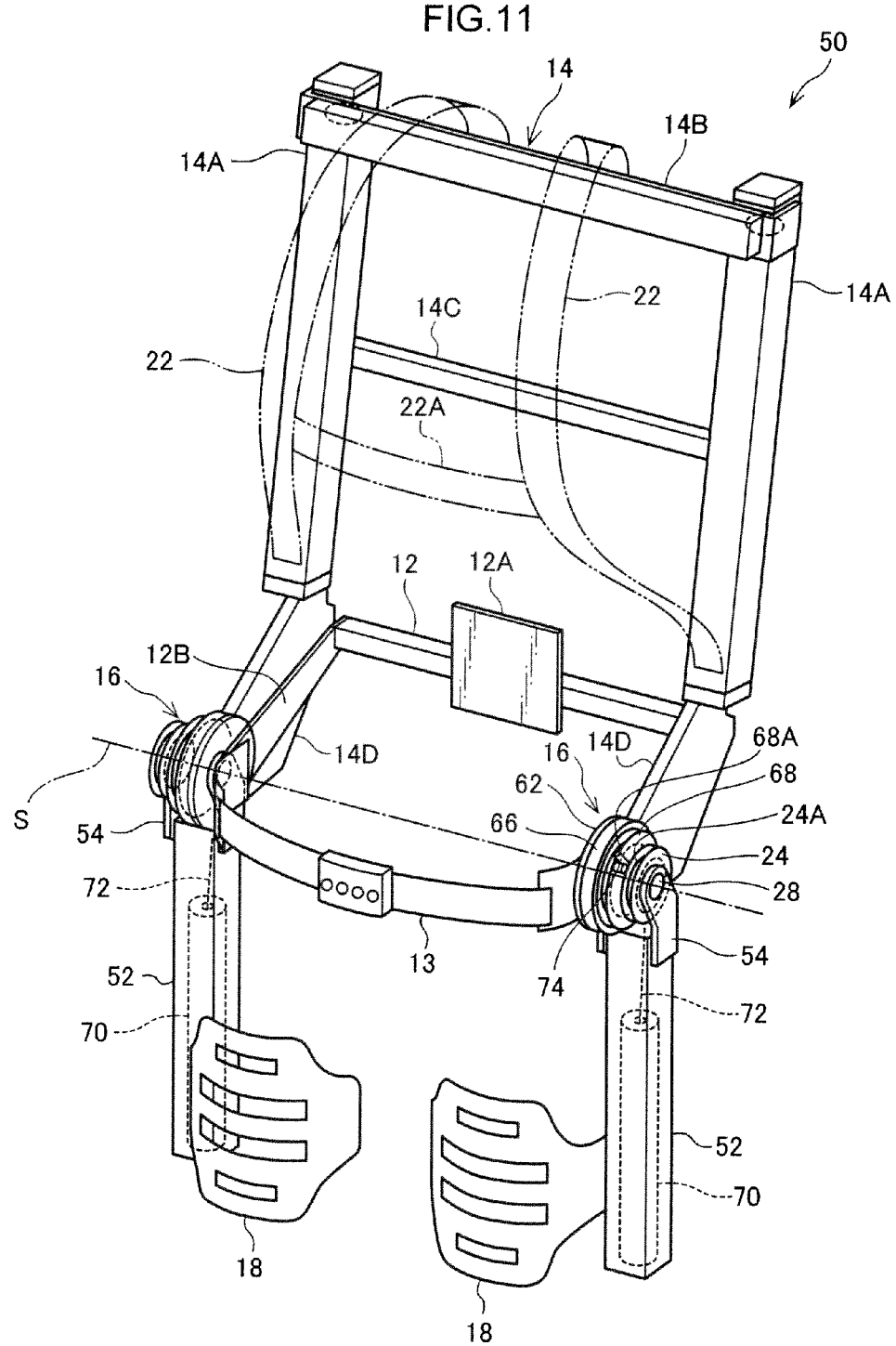
FIG. 11 is a perspective view of a lower back assistance apparatus according to a second exemplary embodiment of the present invention.
Figure 12:
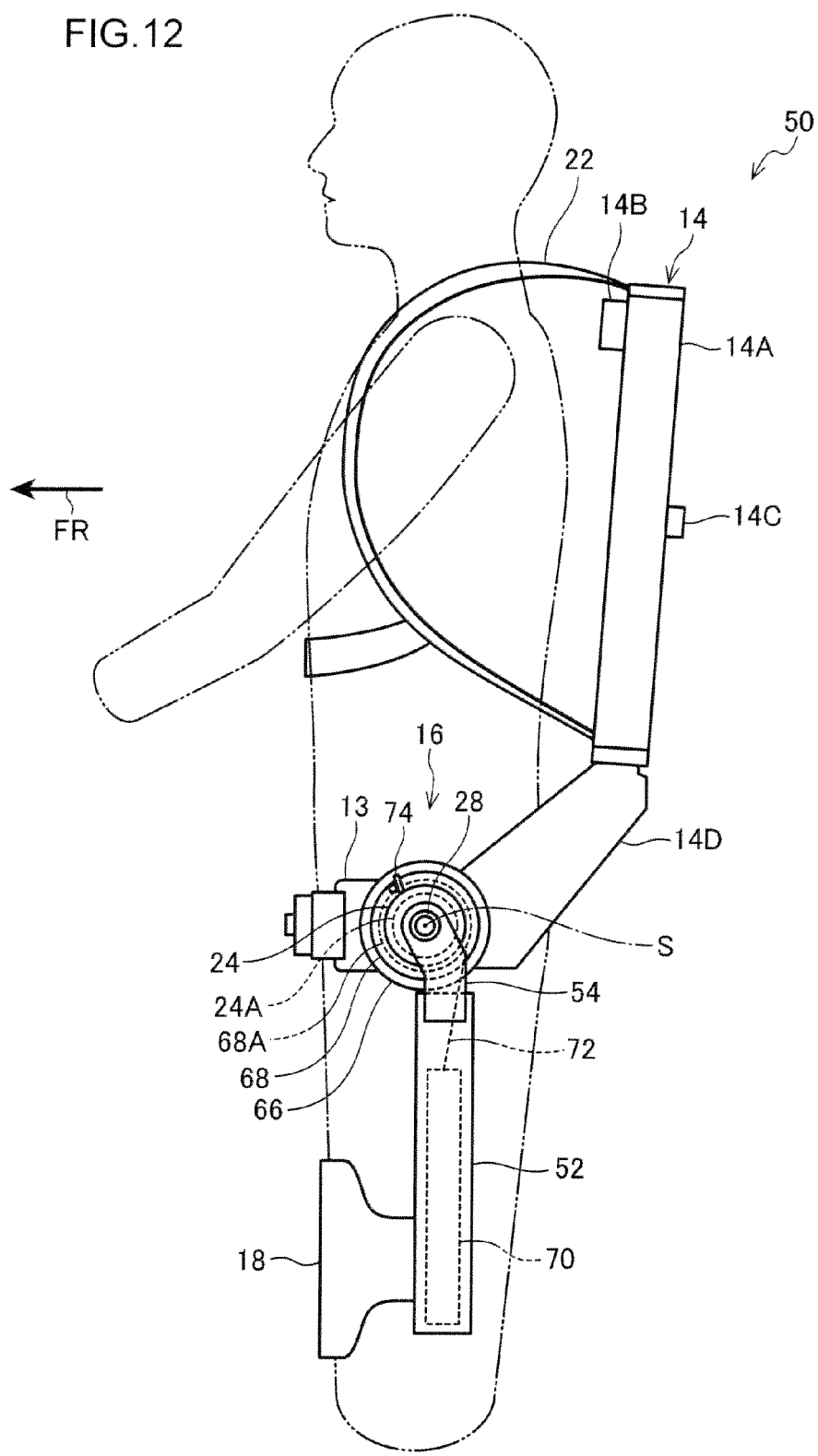
FIG. 12 is a side view illustrating astute of use of a lower back assistance apparatus according to the second exemplary embodiment of the present invention.
Figure 13:
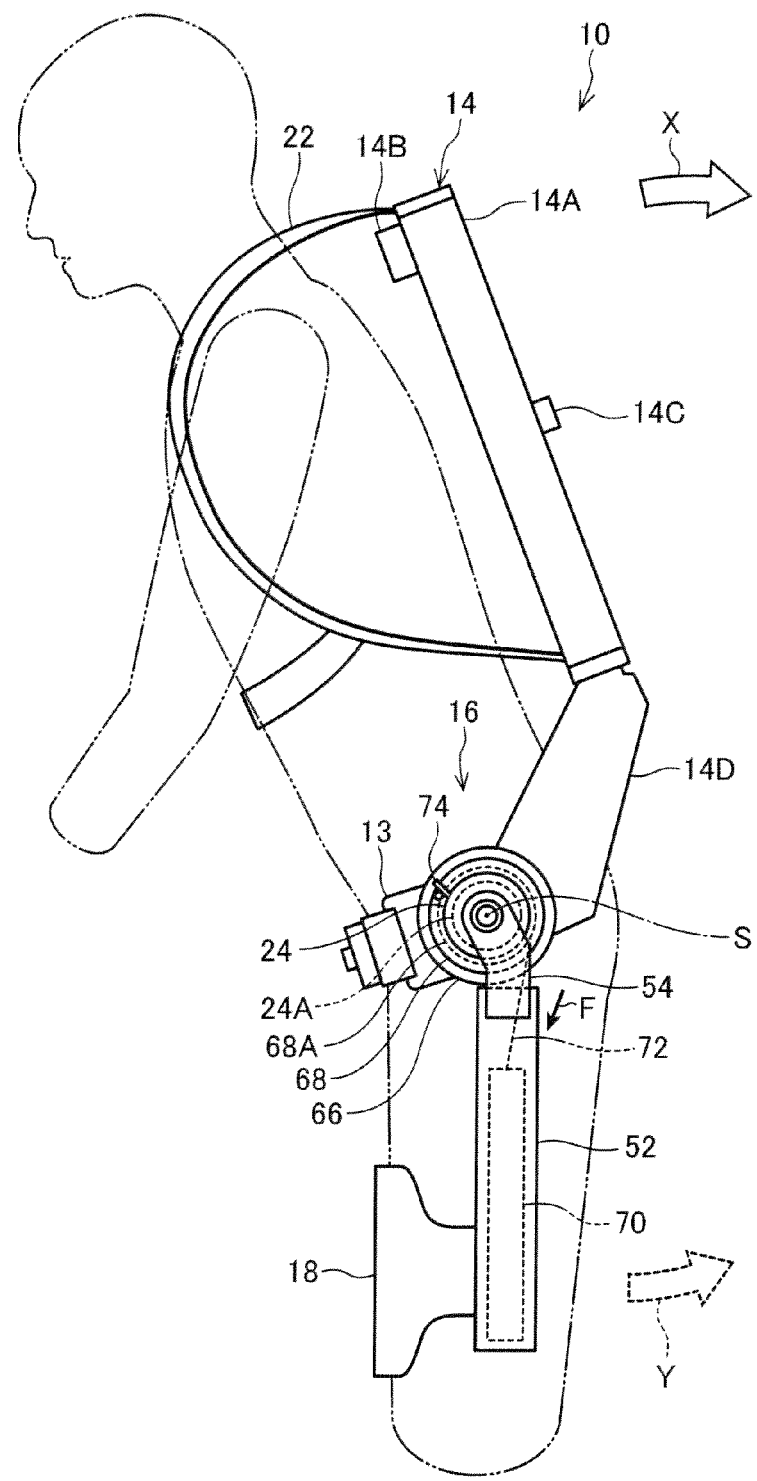
FIG. 13 is a side view illustrating a state of use of a lower back assistance apparatus according to the second exemplary embodiment of the present invention.
Figure 14:
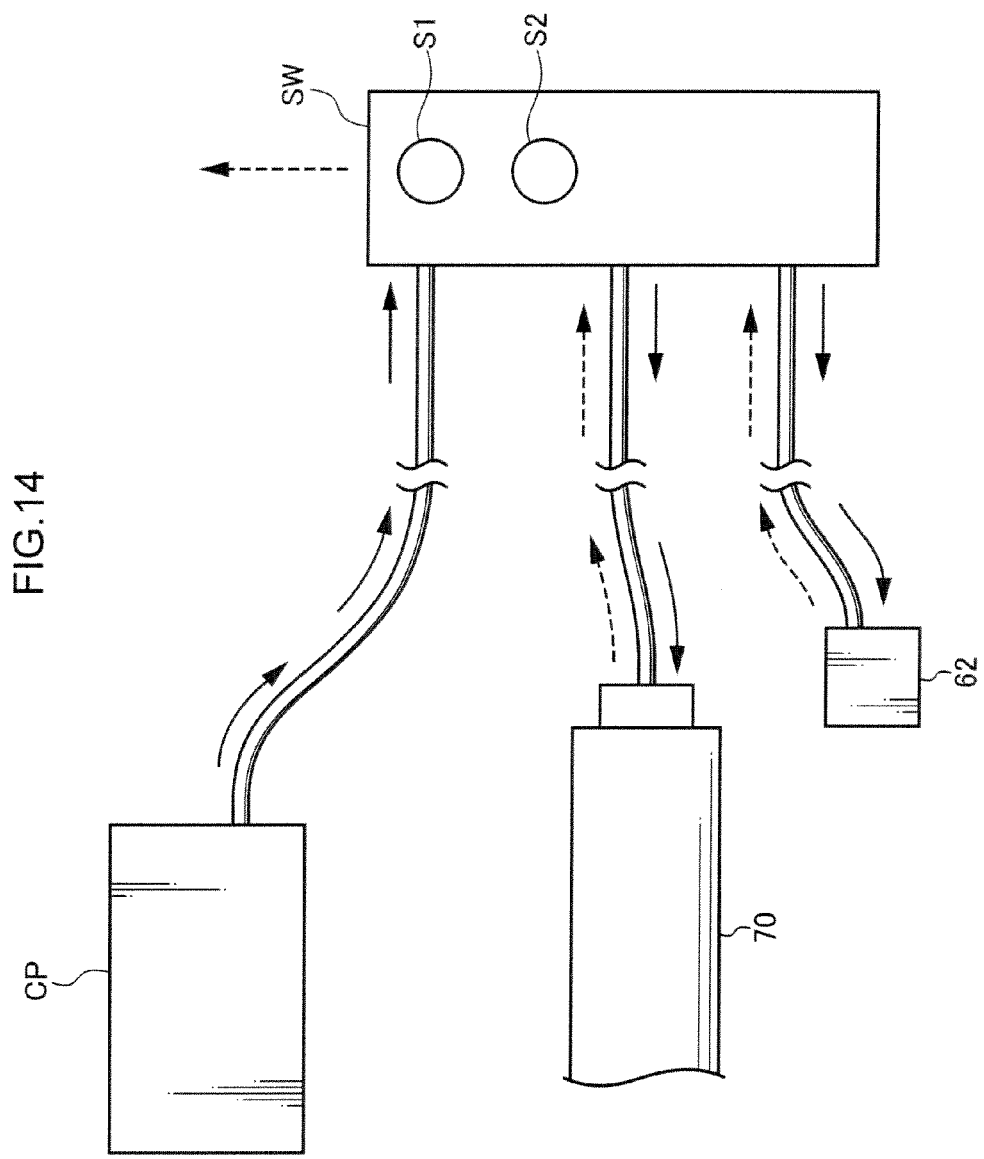
FIG. 14 is a drawing schematically showing an actuator air supply and discharge mechanism provided to a lower back assistance apparatus according to the second exemplary embodiment of the present invention.

As shown in FIG. 11 to FIG. 13, coupling frames 52 are formed from elongated tubes disposed along the lower limbs of a user. A portion at one end of each of the coupling frames 52 is rotatably attached to rotation shafts 28 through an arm 54, and coupled to a lower side section 14D. A thigh plate 18A is attached to a portion at the other end of each of the coupling frames 52. A lower actuator 70 is housed inside the tube of each of the coupling frames 52. The configuration of the lower actuators 70 themselves is similar to the actuators 40. As shown in FIG. 14, a compressor CP is connected to the lower actuators 70 through a switch SW. Compressed air is supplied from the compressor CP to the lower actuators 70 when an air supply switch S1 is switched ON and an air discharge switch S2 is switched OFF. Air is discharged from inside the lower actuators 70 when the air discharge switch S2 is switched ON and the air supply switch S1 is switched OFF.

Wires 72 of the lower actuators 70 extend out from the upper end side of the lower actuators 70. and one end of each of the wires 72 is fixed to a pulley 68, described later.

Figure 15:
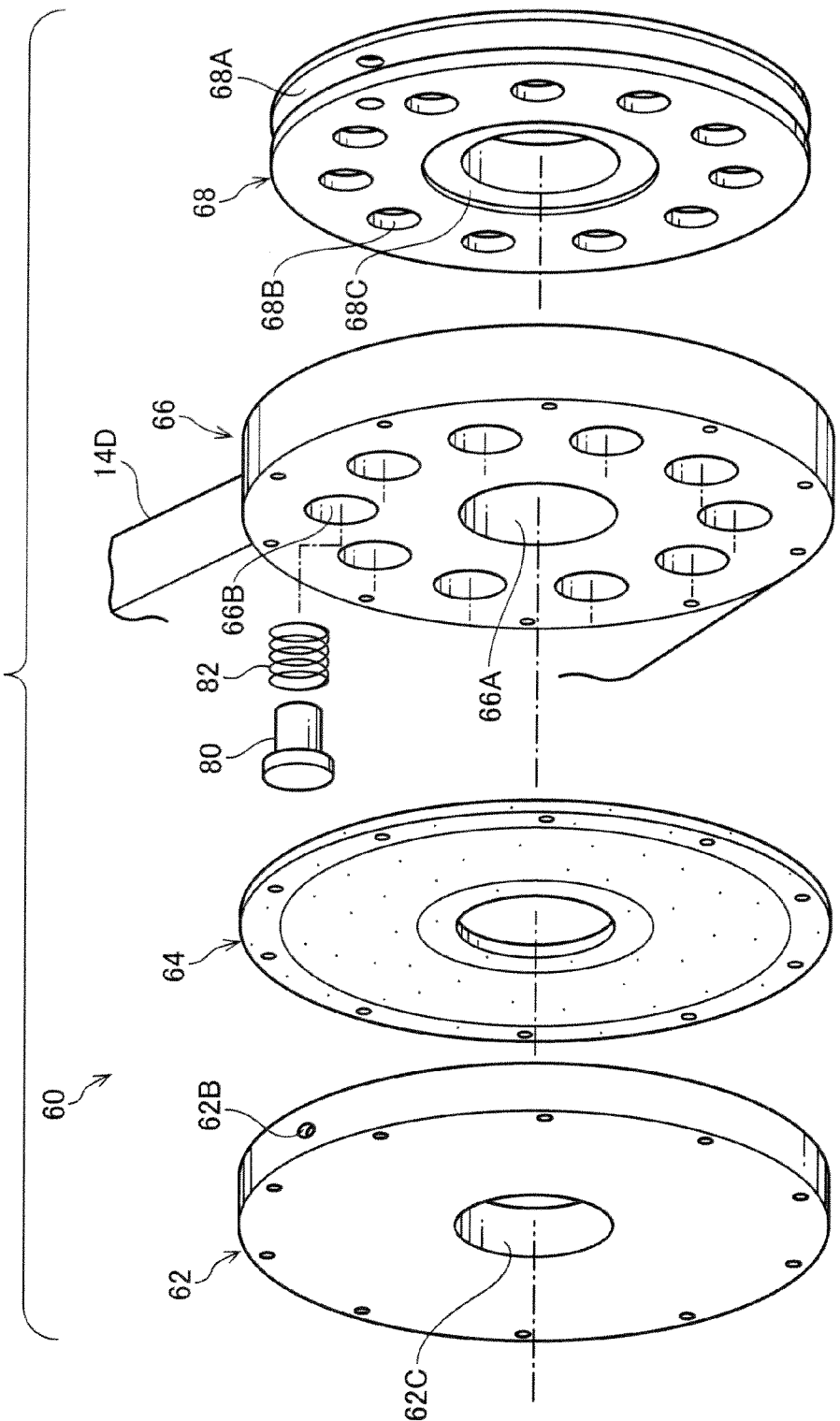
FIG. 15 is an exploded perspective view showing a clutch mechanism of a lower back assistance apparatus according to the second exemplary embodiment of the present invention.

A clutch mechanism 60 is configured to each of left and right joint sections 16. The clutch mechanism 60 is. as shown in FIG. 15, configured including a control air chamber member 62. a diaphragm 64, a plate 66 and a pulley 68.

Figure 17:
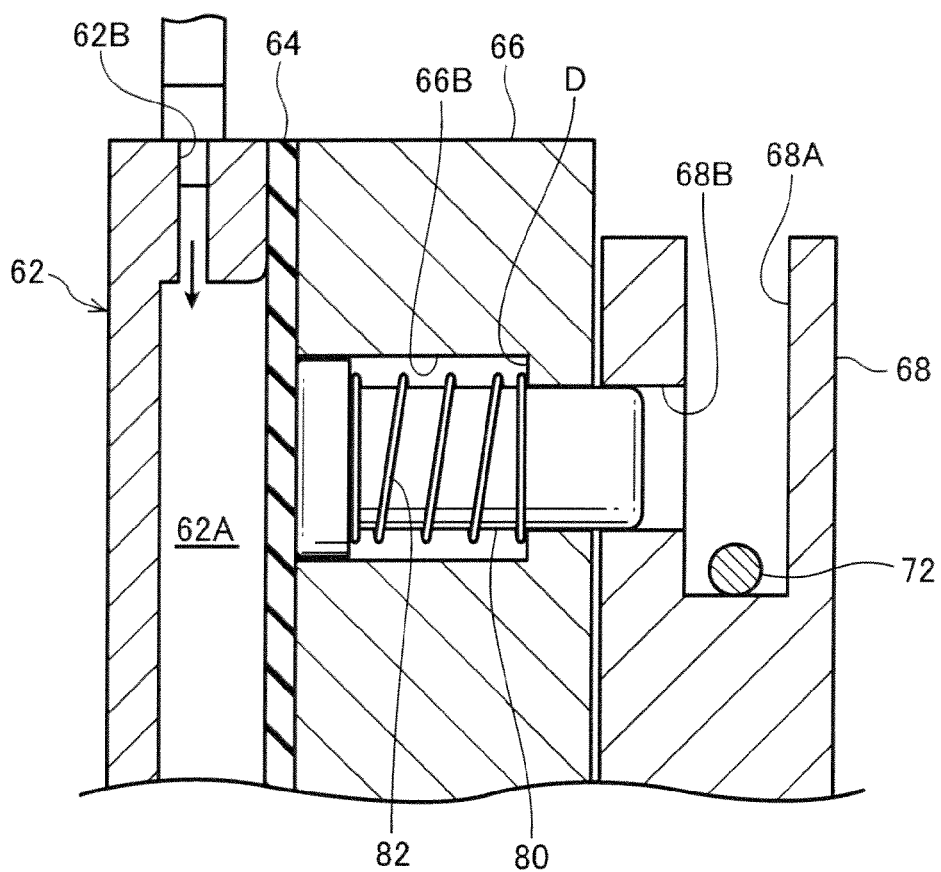
FIG. 17 is across section showing a clutch mechanism of a lower back assistance apparatus according to the second exemplary embodiment of the present invention in a state in which a pulley is fixed to a plate.

The control air chamber member 62 is configured with a control air chamber 62A formed with a substantially circular plate shape having a recessed profile along the circumferential direction of the outside face (see FIG. 6 and FIG. 17). A control air port 62B is pierced as a hole in the outer peripheral face so as to communicate with the control air chamber 62A. The compressor CP is connected to the control air port 62B through the switch SW. Compressed air is supplied from the compressor CP into the control air chamber 62A through the control air port 62B when the air supply switch S1 is switched ON and the air discharge switch S2 is switched OFF. Air inside the control air chamber 62A is discharged when the air discharge switch S2 is switched ON and the air supply switch S1 is switched OFF. An axial hole 62C is pierced through a central portion of the control air chamber member 62, and the rotation shaft 28 is inserted into the axial hole 62C.

The diaphragm 64 is bonded to the outside face of the control air chamber member 62 and configures a portion of the wall face of the control air chamber 62A. The control air chamber 62A is tightly sealed by the diaphragm 64. The diaphragm 64 is configured from a resilient membrane such that the control air chamber 62A is capable of expanding or contracting according to changes in the internal pressure within the control air chamber 62A.

Each of the plates 66 is a substantially circular plate shape fixed to a leading end portion of each of the lower side sections 14D. The plate 66 is disposed at the outside of the diaphragm 64. An axial hole 66A is pierced in a central portion of each of the plates 66, and the rotation shafts 28 are inserted into the axial holes 66A. Ten individual pin holes 66B are pierced in each of the plates 66 at even intervals around a circumferential direction with the axial hole 66A at the center. Each of the pin holes 66B is configured with a step D of slightly reduced diameter D on the pulley 68 side. A pin 80, described later, is inserted through each of the pin holes 66B.

The pulley 68 is formed with a circular plate shape and disposed at the outside face of the plate 66. A groove 68A is configured in the outer periphery of the pulley 68. A thrust bearing 68C is provided at a central portion of the pulley 68. The thrust bearing 68C is attached to the rotation shafts 28 so as to be capable of relative rotation thereto. 11 individual pin holes 68B are pierced in the pulley 68 so as to be arranged in a row along the placement line of the pin holes 66B, with there being a slightly shorter hole separation distance between the pin holes 68B than between the pin holes 66B.

Figure 16:
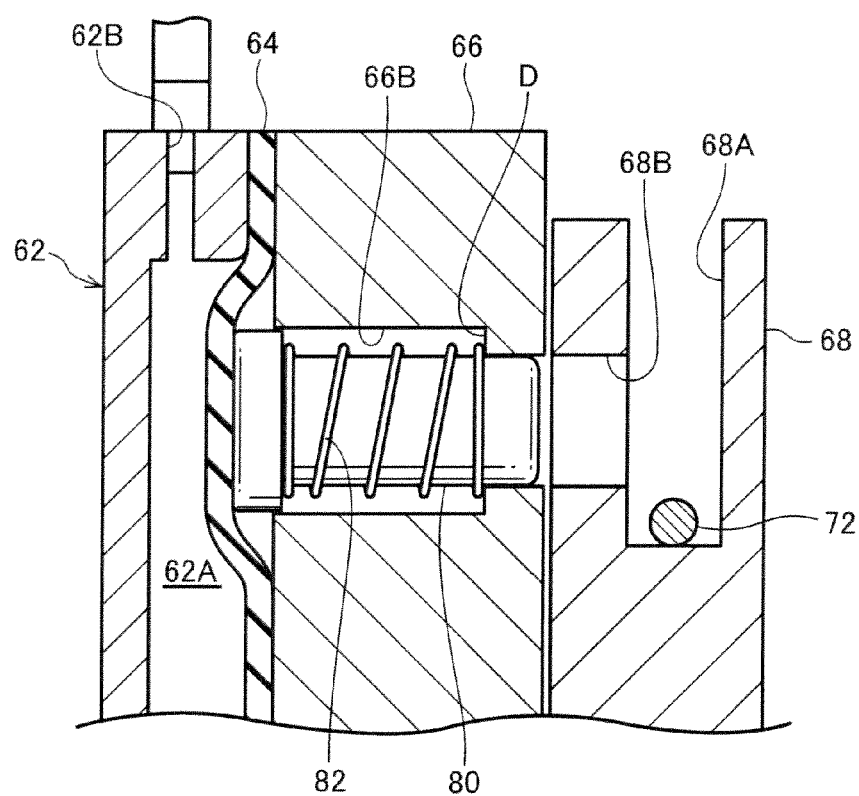
FIG. 16 is across section showing a clutch mechanism of a lower back assistance apparatus according to the second exemplary embodiment of the present invention in a state in which a pulley is not fixed to a plate.

The pins 80 are inserted from the diaphragm 64 side into each of the pin holes 66B. As shown in FIG. 16, a spring 82 is mounted on the outer periphery of each of the pins 80, with one end of each of the springs 82 making contact with the step D. Each of the pins 80 is biased by the spring 82 towards the diaphragm 64 side. Consequently, in a state in which pressing force from the diaphragm 64 is not acting on the pins 80, as shown in FIG. 16, the diaphragm 64 is pressed and deformed towards the control air chamber 62A side, such that the leading end portions of the pins 80 are housed inside the plate 66 and the pins 80 do not project out towards the pulley 68 side. When compressed air is supplied to the control air chamber 62A and the pressure inside the control air chamber 62A is raised, as shown in FIG. 17, the pins 80 are pressed by the diaphragm 64 towards the pulley 68 side, and the leading ends of the pins 80 project out towards the pulley 68 side. A configuration is accordingly achieved in which a very slight amount of rotation of the pulley 68 results in one or other of the pins 80 being inserted into one of the pin holes 68B.

The control air chamber member 62, the diaphragm 64 and the plate 66 are fixed to each of the rotation shafts 28 so as to be able to rotate together with the rotation shafts 28. The pulley 68 is capable of rotation about the rotation shafts 28 in astute in which the pins 80 are not inserted. However the pulley 68 is fixed to the plate 66 so as to rotate together with the rotation shaft 28 when one of the pins 80 is inserted into one of the pin holes 68B. The rotation bodies 24 and the coupling frames 52 are attached to the rotation shafts 28 so as to be relatively rotatable with respect to the rotation shafts 28.

The end portion of each of the wires 72 extending out from the lower actuators 70 is fixed in the groove 68A of the pulley 68, and wound along the groove 68A. The length of the wires 72 is a sufficient length to secure following rotation of the coupling frames 20 in the user forward direction. A tension spring 74 formed for example from a torsion spring is attached between the arm 54 and the pulley 68, biasing the pulley 68 in the anticlockwise direction as viewed from the left hand side. The slack in the wires 72 is accordingly taken up on the pulley 68, resulting in a state in which pretension has been applied to the lower actuators 70. The pretension can enhance the usage efficiency of the actuators by setting to about 5% to 10% of the actuator specification.

Explanation follows regarding operation of the present exemplary embodiment. The back frame 14 follows the forward tilting of the user upper body when a user performs a forward bending action and the back frame 14 tilts forwards. When this occurs the air supply switch S1 of the switch SW is switched OFF, and the back frame 14 and the coupling frames 52 rotated relative to each other about the rotation axis S of the joint sections 16. The back frame 14 and the coupling frames 52 are uncoupled from each other by the clutch mechanism 60 during such relative rotation, enabling the back frame 14 to freely follow forward tilting.

In the forward tilted state of the back frame 14, air is supplied to the lower actuators 70 and to the control air chamber 62A when the air supply switch S1 is switched ON and the air discharge switch S2 is switched OFF. The lower actuators 70 accordingly contract. A high internal pressure of the control air chamber 62A is achieved, and the diaphragm 64 deforms from the state illustrated in FIG. 16 to the state illustrated in FIG. 17, such that one of the pins 80 is inserted into one of the pin holes 68B of the pulley 68. The pulley 68 is accordingly fixed to the plate 66 and unwinding of the wires 72 is restricted. Accordingly. due to combination with the action of the tension spring 74, the lower actuators 70 are capable of generating tension force F on the wires 72 from the time of contraction initiation.

A force arising from the tension force F acts to rotate the coupling frames 52 about the rotation axis S in the rotation direction Y, and a force acts to rotate the back frame 14 about the rotation axis S in the rotation direction X, the opposite to that of the coupling frames 52. When this occurs a force acts through the shoulder straps 22 on the upper body of a forward tilted user in the raising rotation direction X. A user can accordingly be assisted in an action to raise their upper body. The effort required when in a forward tilting posture can also be reduced, enabling a forward tilting posture to be maintained with ease. When the force in the raising rotation direction X becomes larger than the force tilting a user forwards, the back frame 14 is rotated in the raising rotation direction X and the upper body of a user can be raised.

Air supply to the actuators ceases when the air supply switch S1 is switched OFF and the air discharge switch S2 is switched OFF, the air pressure inside the lower actuators 70 and inside the control air chamber 62A ceases to rise, and contraction of the lower actuators 70 stops. The back frame 14 stops moving in such a state.

When the weight of the upper body of the forward tilting user is entrusted to the shoulder straps 22 in this state (the forward tilted upper body is rested against the shoulder straps 22), the upper body adopts a state in which it hangs from the back frame 14. Consequently. the user is able to maintain the forward tilting posture without using the muscles in their lower back (such as the erector spinae). Assistance to maintaining the user forward tilting posture is achieved by maintaining contraction of the actuators 70.

According to the present exemplary embodiment, due to provision of the clutch mechanisms 60 including the tension springs 74, the pulleys 68 wound with the wires 72 are fixed to the plate 66 during actuation of the lo actuators 70. Unwinding of the wires 72 from the lower actuators 70 is accordingly restricted, and the tension force F can be generated immediately after actuating the lower actuators 70.

Figure 18:
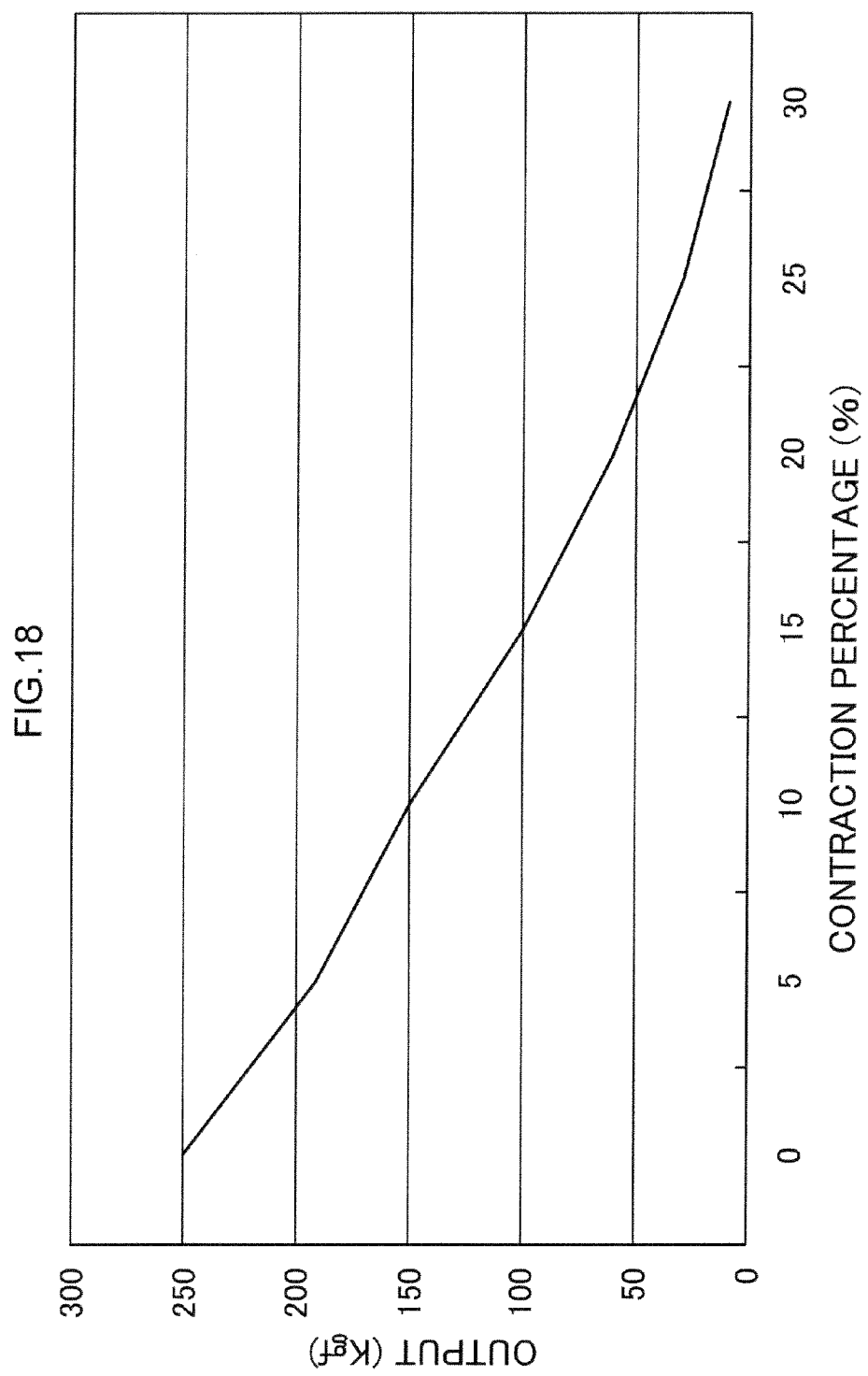
FIG. 18 is a graph showing a relationship between the contraction percentage and output of a pneumatic actuator.

Explanation follows regarding action characteristics of general pneumatic actuators. FIG. 18 is a graph illustrating a relationship between contraction percentage and output power for a pneumatic actuator. It is clear from the graph that since output power falls as the contraction percentage of the pneumatic actuators rises, a large load needs to be taken during the initial contraction action in order to employ a pneumatic actuator efficiently.

In the present exemplary embodiment, as explained above, any slackness in the wires is removed by the tension spring 74, enabling the tension force F to be generated on the wires 72 immediately after actuation of the lower actuators 70. Hence, the lower actuators 70 can be employed with good efficiency since the amount of contraction to take up the length of play in the wires 72 is no longer required for the lower actuators 70.

In the present exemplary embodiment, the clutch mechanisms 60 are provided to generate the tension force F in the wires 72 during actuation of the lower actuators 70, however a similar configuration to that of the clutch mechanism 60 can also be appropriately applied to the actuators 40 side in the first exemplary embodiment.

Figure 19:
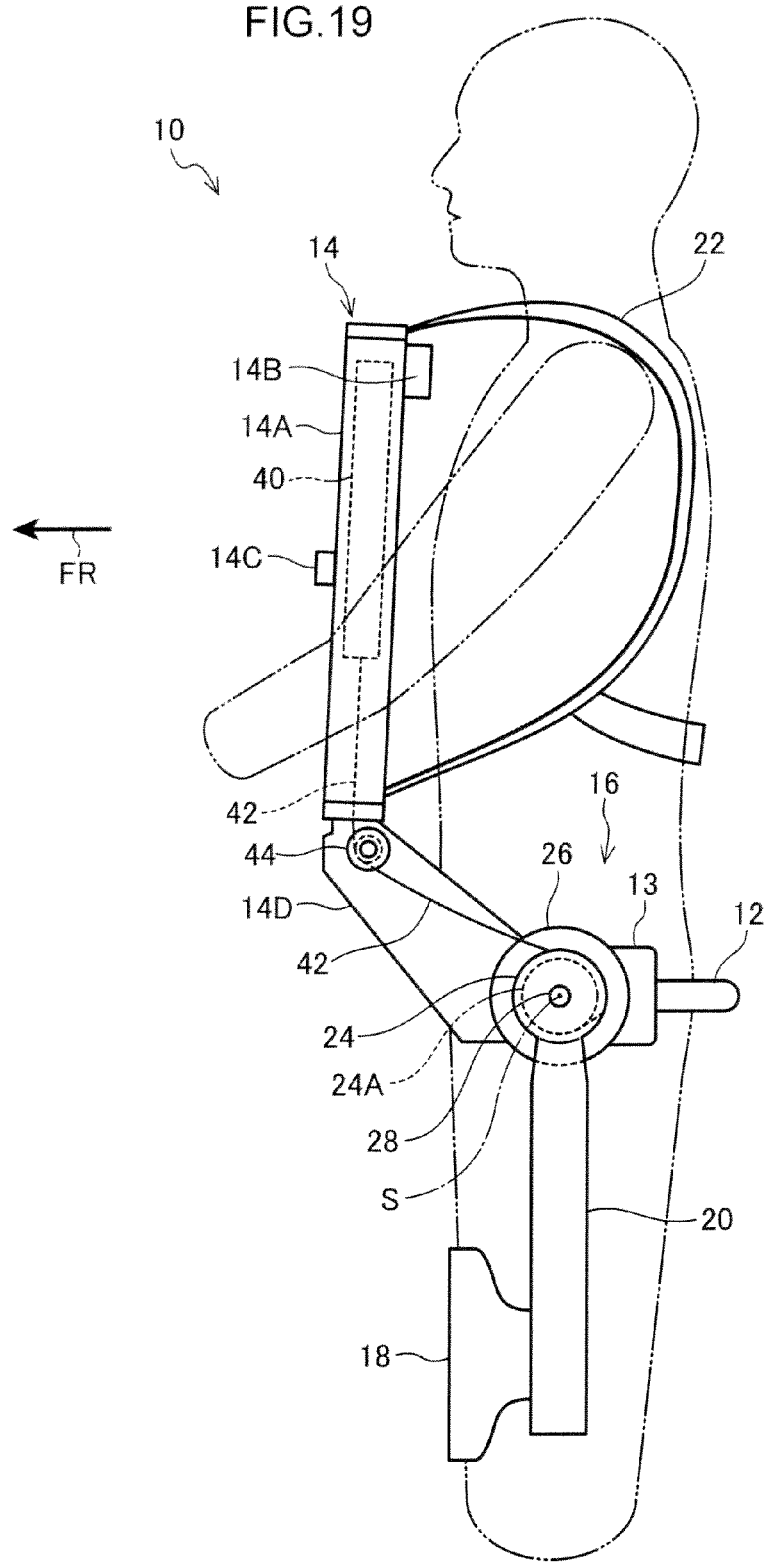
FIG. 19 is a side view illustrating a state of use of a lower back assistance apparatus according to a modified example of the first exemplary embodiment and the second exemplary embodiment of the present invention.

In the first exemplary embodiment and the second exemplary embodiment described above the back frame 14 is employed as the upper body mounting section mounted to the back of a user, however configuration may be made, as shown in FIG. 19, with a chest frame 21 for mounting to the chest of a user.

Third Exemplary Embodiment

Explanation follows regarding a third exemplary embodiment of the present invention. Parts of the configuration similar to those of the first exemplary embodiment and the second exemplary embodiment are allocated the same reference numerals and detailed explanation thereof is omitted.

Figure 20:
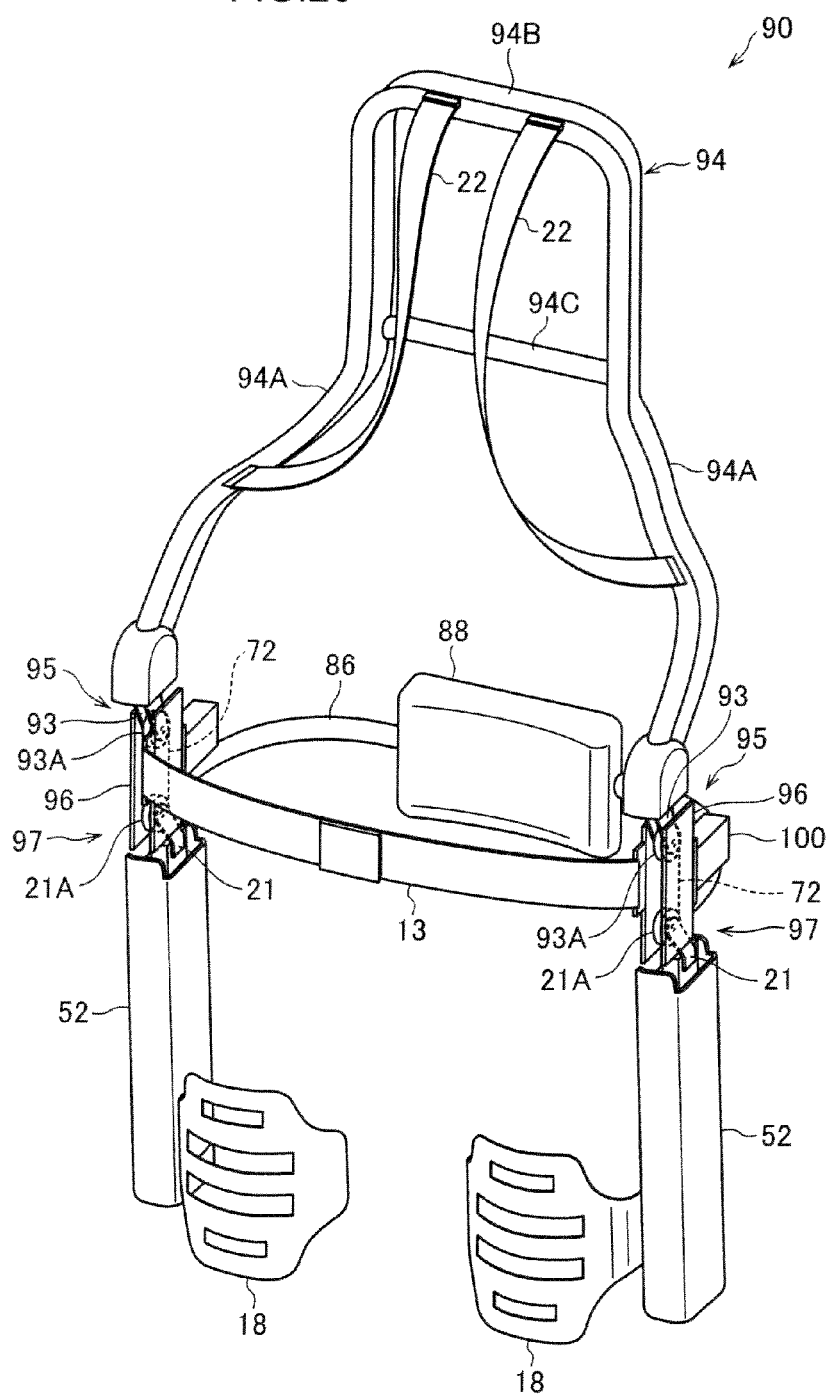
FIG. 20 is a perspective view of a lower back assistance apparatus according to a third exemplary embodiment of the present invention.
Figure 21:
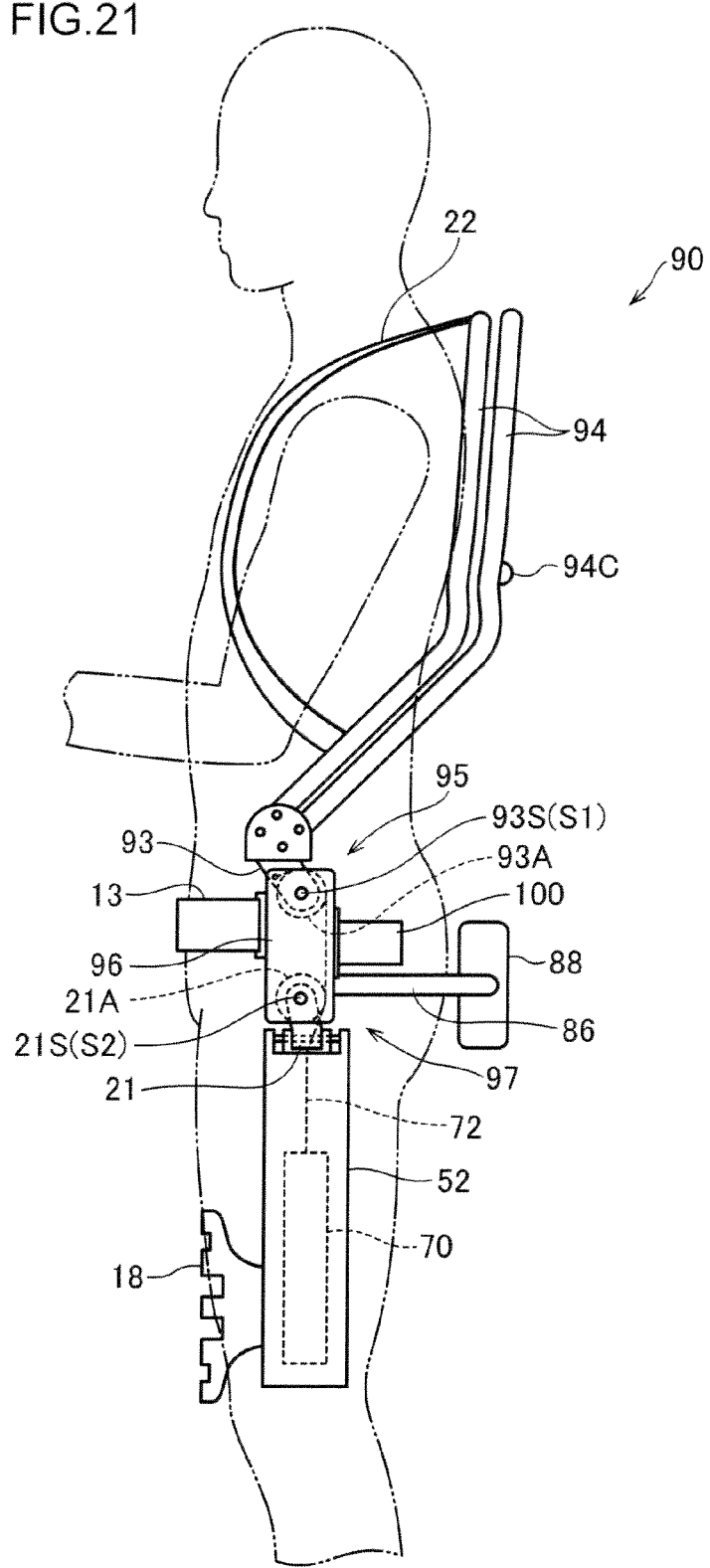
FIG. 21 is a side view illustrating a state of use of a lower back assistance apparatus according to the third exemplary embodiment of the present invention.
Figure 22:
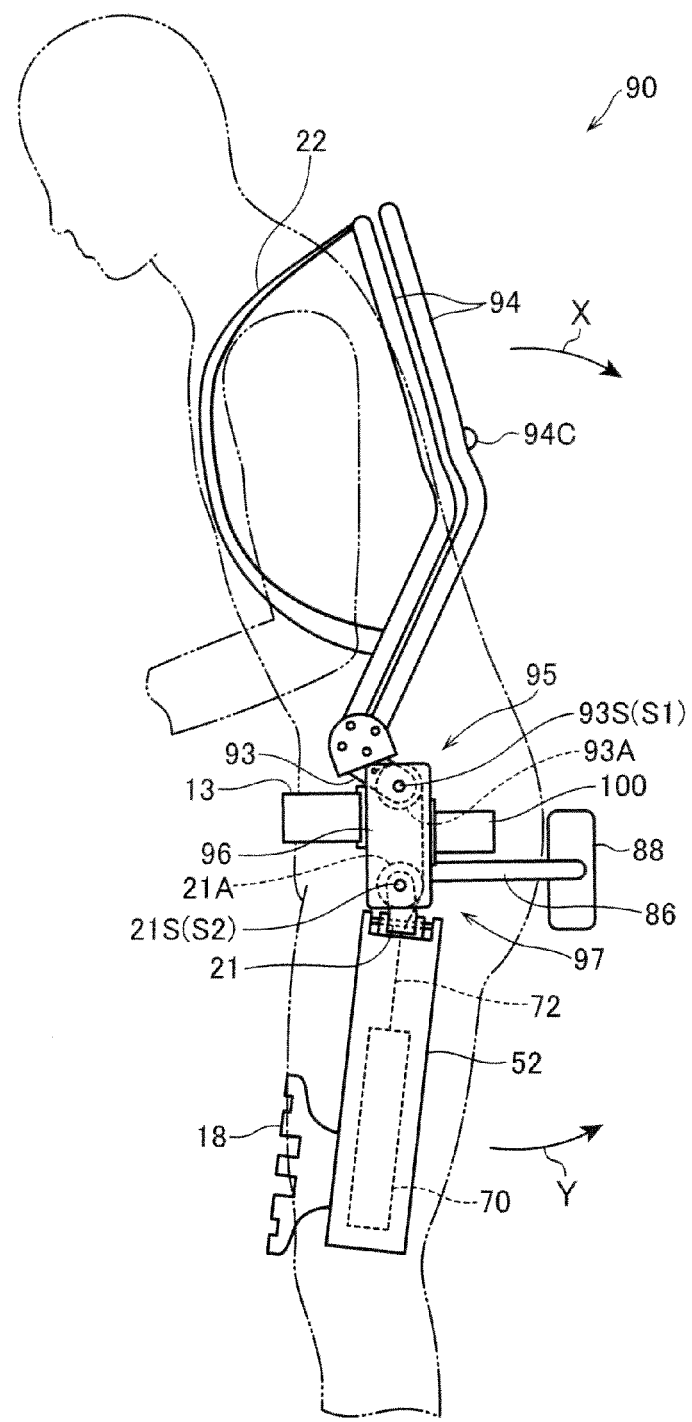
FIG. 22 is a side view illustrating a state of use of a lower back assistance apparatus according to the third exemplary embodiment of the present invention.

FIG. 20 to FIG. 22 illustrate a lower back assistance apparatus 90 according to a third exemplary embodiment. FIG. 20 illustrates the lower back assistance apparatus 90 in a pre-mounted state, and FIG. 21 and FIG. 22 illustrate the lower back assistance apparatus 90 in a state mounted to a user. As shown in these drawings, the lower back assistance apparatus 90 includes a back frame 94 serving as an upper body mounting section, shoulder straps 22 serving as front support sections, thigh plates 18 serving as lower limb mounting sections, upper coupling frames 96 serving as coupling sections and coupling frames 52.

The back frame 94 is mounted to the back of a user and includes a left and right pair of side frame sections 94A, and center frame sections 94B, 94C for coupling together the left and right pair of side frame sections 94A. The left and right side frame sections 94A and the center frame section 94B are configured as a single unit. The center frame section 94C is disposed so as to couple together intermediate portions of the left and right side frame sections 94A.

A first joint section 95 is configured at the lower end of each of the left and right side frame sections 94A. The back frame 94 and the upper coupling frames 96 are coupled together with the first joint sections 95. A waist belt 13 is provided at the front of the first joint sections 95. The waist belt 13 is disposed in front of the waist of a user, spanning across between the left and right pair of upper coupling frames 96 so as to couple the upper coupling frames 96 together.

The upper coupling frames 96 are formed in elongated plate shapes disposed with their length directions along the hips of a user so as to be aligned in the up-down direction. The back frame 94 (the left and right side frame sections 94A) is coupled through plates 93, described later, to the upper coupling frames 96 at the upper end sides of the upper coupling frames 96, such that relative rotation of the back frame 94 to the upper coupling frames 96 is possible about a rotation axis S1 running along the user left-right direction. The upper coupling frames 96 are configured by rigid members that do not bend even when rotated relative to the back frame 94.

Second joint sections 97 are configured at the bottom ends of the upper coupling frames 96. The upper coupling frames 96 and the coupling frames 52 are coupled together at the second joint sections 97 through a plate 21, described later. The upper coupling frames 96 and the coupling frames 52 are coupled together so as to capable of relative rotation with respect to each other about a rotation axis S2 running along the user left-right direction. The coupling frames 52 are configured by rigid members that do not bend even when rotated relative to the upper coupling frames 96.

Thigh plates 18 are fixed to the side of the coupling frames 52 at the other end. The thigh plates 18 are disposed in front of the lower limbs of a user.

Figure 23:
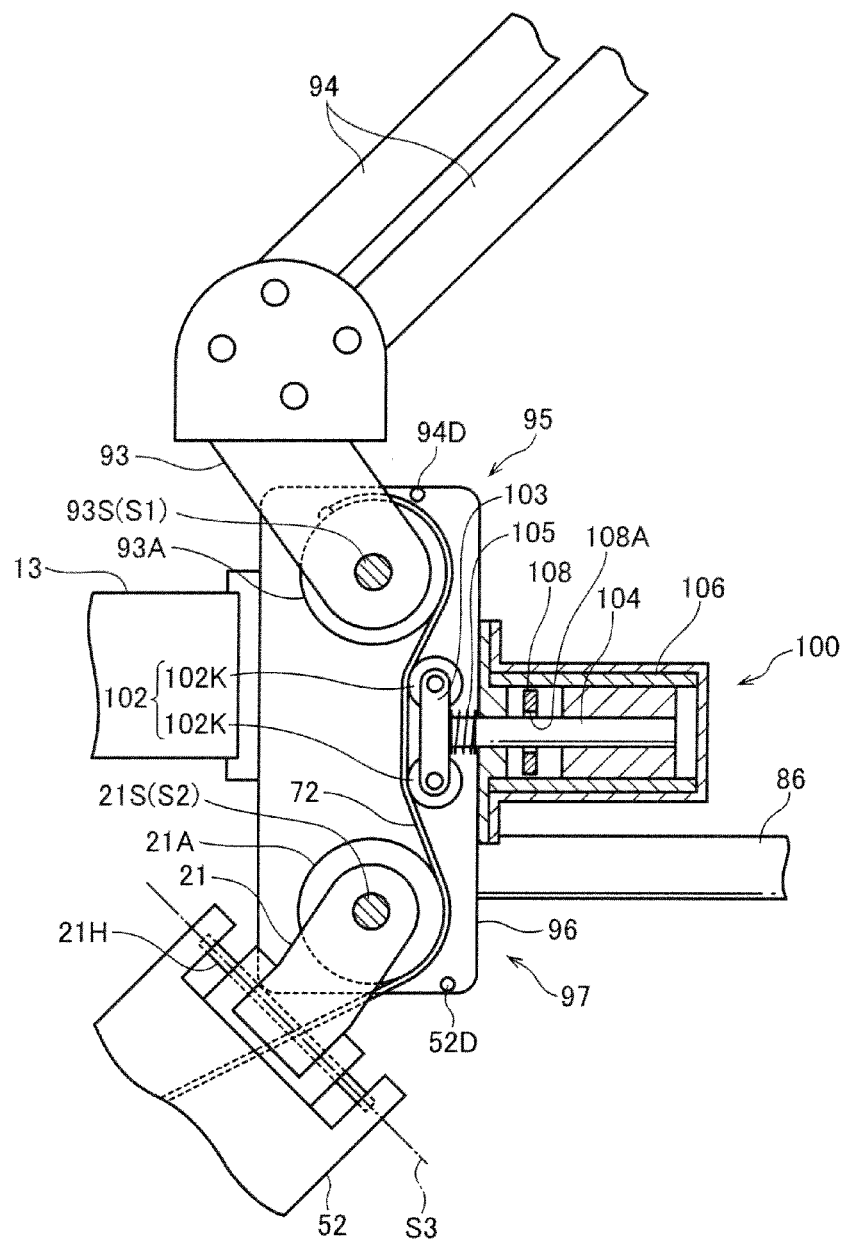
FIG. 23 is an expanded drawing of the vicinity of a clutch section according to the third exemplary embodiment of the present invention.

As shown in FIG. 22 and FIG. 23, each of the first joint sections 95 includes a plate 93 fixed to a lower end portion of the respective left and right side frame sections 94A, a rotation shaft 93S that projects out from the plate 93 towards the shoulder width direction outside (or inside), and a rotation body 93A that is formed in a circular plate shape and is rotatably supported on the rotation shaft 93S. The left and right pair of first joint sections 95 are configured so as to be left-right symmetrical to each other.

The plates 93 are disposed at the sides of the lumbar region of a user, with each of the rotation shafts 93S extending out in a direction from the user lumbar region side towards the shoulder width direction outside. Circular holes (not shown in the drawings) are formed at the axial center of the rotation bodies 93A for fitting the rotation shafts 93S into such that relative rotation is possible. A groove (not shown in the drawings) is formed in the peripheral face of each of the rotation bodies 93A to enable the wires 72 to be wrapped around.

The rotation bodies 93A are fixed to the upper coupling frames 96, such that the upper coupling frames 96 and the rotation bodies 93A are capable of relative rotation with respect to the plates 93 and the back frame 94.

Stopper members 94D are provided at the upper side of the upper coupling frames 96, on the user rearward side. The stopper members 94D project out from the inside of the upper coupling frames 96 along the user left-right direction. The stopper members 94D make contact with the plates 93 when the upper coupling frames 96 have rotated in the arrow Y direction together with the back frame 94 rotating in the arrow X direction so as to approach each other to a specific angle. The stopper members 94D have a function of preventing rotation exceeding the specific angle.

Each of the second joint sections 97 includes a plate 21 attached to a portion at the upper end of the coupling frame 52, a rotation shaft 21S that projects out from the plate 21 towards the shoulder width direction outside (or inside), and a rotation body 21A formed in a circular plate shape and rotatably supported on the rotation shaft 21S. The left and right pair of second joint sections 97 are configured so as to be left-right symmetrical to each other.

The plates 21 are placed outside the hip joints of a user and the rotation shafts 21S extend out towards the user shoulder width direction outside. Circular holes (not shown in the drawings) are formed at the axial center of the rotation bodies 21A for fitting the rotation shafts 21S into such that relative rotation is possible. A groove (not shown in the drawings) is formed in the peripheral face of each of the rotation bodies 21A to enable the wires 72 to be wrapped around.

The rotation bodies 21A are fixed to the upper coupling frames 96, and the upper coupling frames 96 and the rotation bodies 21A are capable of relative rotation with respect to the plate 21 and the coupling frames 52.

Stopper members 52D are provided at the lower side of the upper coupling frames 96, on the user rearward side. The stopper members 52D project out from the inside of the upper coupling frames 96 along the user left-right direction. The stopper members 52D make contact with the plates 21 when the upper coupling frames 96 have rotated in the arrow X direction together with the coupling frames 52 rotating in the arrow Y direction no as to approach each other to a specific angle. The stopper members 52D have a function preventing rotation exceeding the specific angle.

Each of the coupling frames 52 is coupled to the plate 21 through a hinge 21H. The hinge 21H enables relative rotation of the coupling frames 52 with respect to the upper coupling frames 96 about a rotation axis S3 disposed in a direction parallel to the body side of a user. The coupling frames 52 are accordingly able to follow opening and closing of the thighs of a user.

A buttock frame section 86 is attached to the upper coupling frames 96. The buttock frame section 86 is disposed across from one of the upper coupling frames 96 to the other of the upper coupling frames 96 around the rear of the buttocks of the user. A buttock plate 88 is attached at a central portion of the buttock frame section 86 so as to face towards the position of the buttocks of a user.

Lower actuators 70 are provided to the lower back assistance apparatus 90. The lower actuators 70 are disposed at the coupling frames 52 side, similarly to in the second exemplary embodiment. Wires 72 are attached to the upper end side of the lower actuators 70. Portions at one end of the wires 72 project out from the upper end of the lower actuators 70, are wrapped around the rotation bodies 21A, are wrapped around the rotation bodies 93A via clutch sections 100, described later, and are fixed in grooves of the respective rotation bodies 93A.

Figure 24:
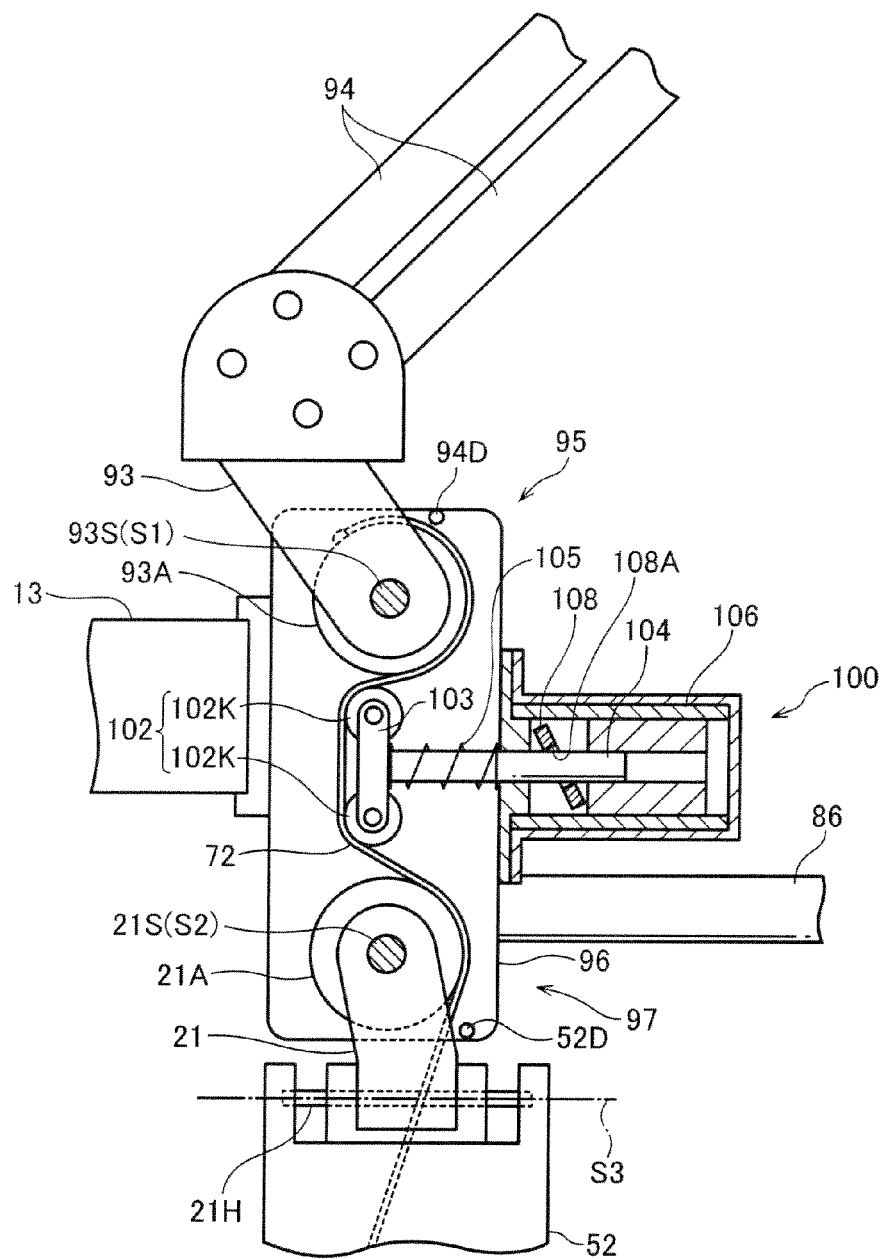
FIG. 24 is an expanded drawing of the vicinity of a clutch section according to the third exemplary embodiment of the present invention.

As shown in FIG. 23 and FIG. 24, the clutch sections 100 are provided to the upper coupling frames 96, and each includes a double block section 102, a piston section 104, a cylinder section 106, and a lock section 108. The cylinder section 106 is fixed to a central portion of the upper coupling frame 96 on the user rearward side. The lock section 108 is disposed inside the cylinder section 106 and has a lock hole 108A provided in the center. The piston section 104 is inserted into the lock hole 108A. Each of the piston sections 104 is disposed along a direction cutting across between the rotation bodies 93A and the rotation bodies 21A, and movement along this direction is possible when the clutch sections 100 are not actuated. The double block section 102 is attached through a support plate 103 to the leading end side of the piston section 104 such that two individual blocks 102K straddle the piston section 104. The double block section 102 is capable of moving together with the piston section 104. Each of the wires 72 is wrapped around both of the respective two individual blocks 102K so as to span between the two.

A coil spring 105 is disposed between the support plate 103 and the cylinder section 106 of the piston section 104. Each of the piston sections 104 is biased towards the user forward direction by the coil spring 105. The wires 72 are accordingly entrained without slack around the rotation bodies 21A, the blocks 102K and the rotation bodies 93A.

The piston section 104 is free to move inside the lock hole 108A when the actuators 40 are not being actuated, enabling movement along the user front-rear direction. However during actuation of the lower actuators 70 the lock section 108 is tilted by controlling the air pressure in the space either to the right or left of the lock section 108, and a one-way check function of the lock section 108 is exhibited. Control is accordingly achieved in which movement is possible in the direction towards the user front (the direction to remove wire slack) but movement in the reverse direction is not possible.

Figure 25:
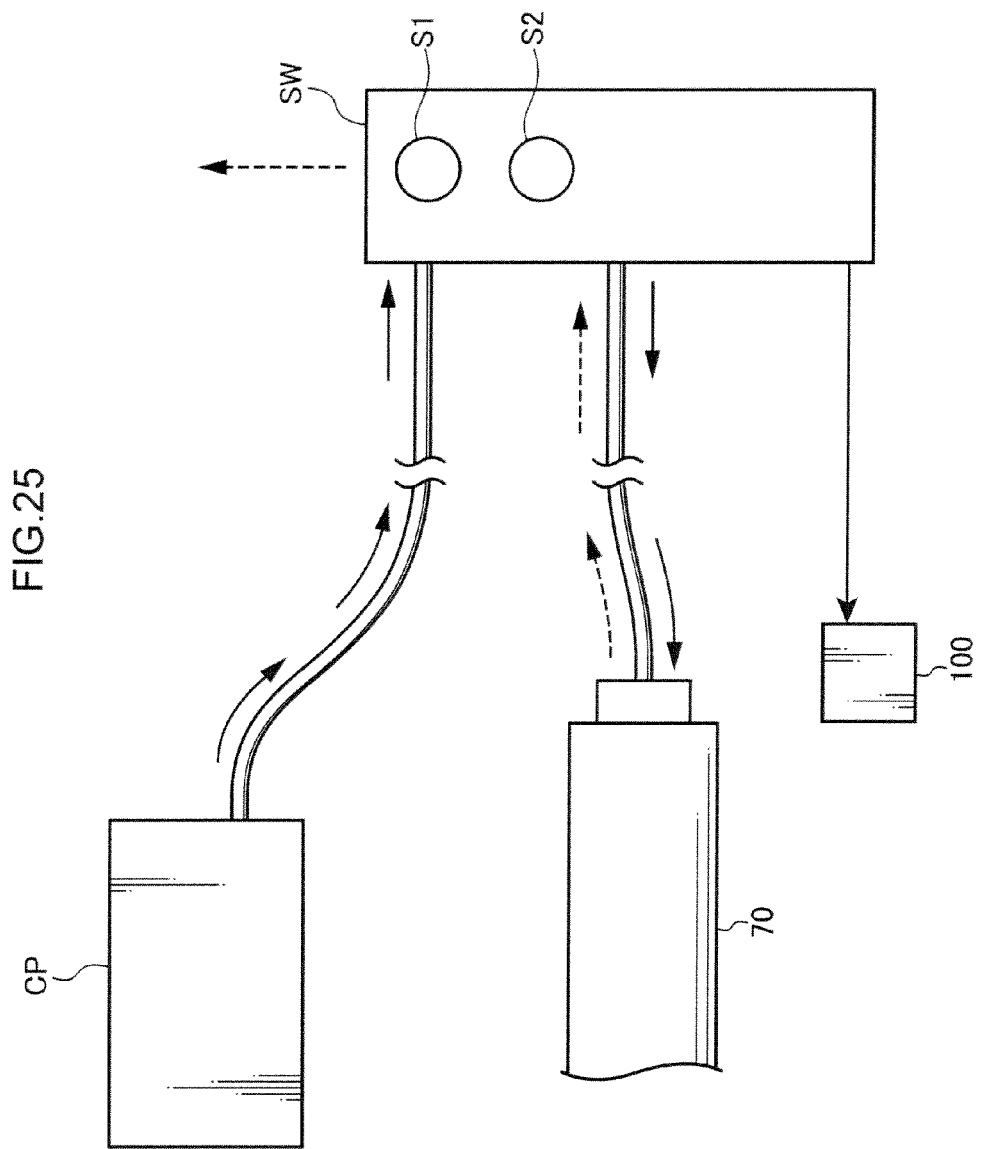
FIG. 25 is a drawing schematically showing an actuator air supply and discharge mechanism provided to a lower back assistance apparatus according to the third exemplary embodiment of the present invention.

As shown in FIG. 25, the compressor CP is connected to the lower actuators 70 through the switch SW. The switch SW is also connected to the clutch sections 100. Compressed air is supplied from the compressor CP to the lower actuators 70 when the air supply switch S1 is switched ON and the air discharge switch S2 is switched OFF, and the one-way check function of the clutch sections 100 is switched ON. Air inside the lower actuators 70 is discharged and the one-way check function of the clutch sections 100 is switched OFF when the air discharge switch S2 is switched ON and the air supply switch S1 is switched OFF. A switch may be independently provided for controlling air to the clutch sections 100.

Explanation follows regarding operation of the present exemplary embodiment. The back frame 94 follows forward tilting of the upper body of the user when a user performs a forward bending action, and the back frame 94 tilts forward. When this occurs the air supply switch 51 of the switch SW is switched OFF, and the back frame 94 and the upper coupling frames 96 rotate relative to each other about the rotation axis S1 of the first joint sections 95. The upper coupling frames 96 and the coupling frames 52 also rotate relative to each other about the rotation axis S2 of the second joint sections 97. During such relative rotation the piston section 104 of each of the clutch sections 100 is able to move so as to retreat towards the rear (move towards the user rearwards direction), and the wires 72 are payed out, enabling the back frame 94 to freely follow the forward tilting (see FIG. 23).

When the air supply switch S1 is switched ON and the air discharge switch S2 is switched OFF in the forward tilted state of the back frame 94, air is supplied to the lower actuators 70, and the inside of the cylinder section 106 is pressurized together with switching ON the one-way check function of the clutch sections 100. The piston section 104 is accordingly pressed towards the user forward direction, rendering movement forwards possible but movement backwards not possible, and slack in the wires 72 is removed (see FIG. 24). Consequently, the tension force F can be generated to the wires 72 from the time of contraction initiation when the lower actuators 70 are contracted.

Force arising from the tension force F acts on the coupling frames 52 in the rotation direction Y about the two axes of the rotation axes S1, S2. and force acts on the back frame 94 in the reverse rotation direction X to that of the coupling frames 52 about the two axes of the rotation axes S1, S2. When this occurs a force acts through the shoulder straps 22 on the upper body of the forward tilting user in the raising rotation direction X, enabling the action of the user to raise their upper body to be assisted. The effort required when in a forward tilting posture is also reduced, enabling a forward tilting posture to be maintained with ease. By making the force in the raising rotation direction X larger than the tilting force towards the user forward direction the back frame 94 can be rotated in the raising rotation direction X and the upper body of a user can be raised.

Air ceases to be supplied into the actuators when the air supply switch S1 is switched OFF and the air discharge switch 82 is switched OFF, such that the air pressure within the lower actuators 70 ceases to rise and contraction of the lower actuators 70 stops. The back frame 94 accordingly stops in such a state.

When the weight of the upper body of the forward tilting user is entrusted to the shoulder straps 22 in this state (the forward tilted upper body is rested against the shoulder straps 22), the upper body adopts a state in which it hangs from the back frame 94. Consequently, the user is able to maintain the forward tilting posture without using the muscles in their lower back (such as the erector spinae). By maintaining contraction of the actuators 70 assistance to maintaining the user forward tilting posture is achieved.

In the present exemplary embodiment, similarly to in the second exemplary embodiment, the tension force F to the wires 72 can be generated immediately after actuation of the lower actuators 70 due to provision of the clutch sections 100. Hence the lower actuators 70 can be efficiently employed since contraction is not required in the lower actuators 70 to take up a length of play in the wires 72.

Figure 26:
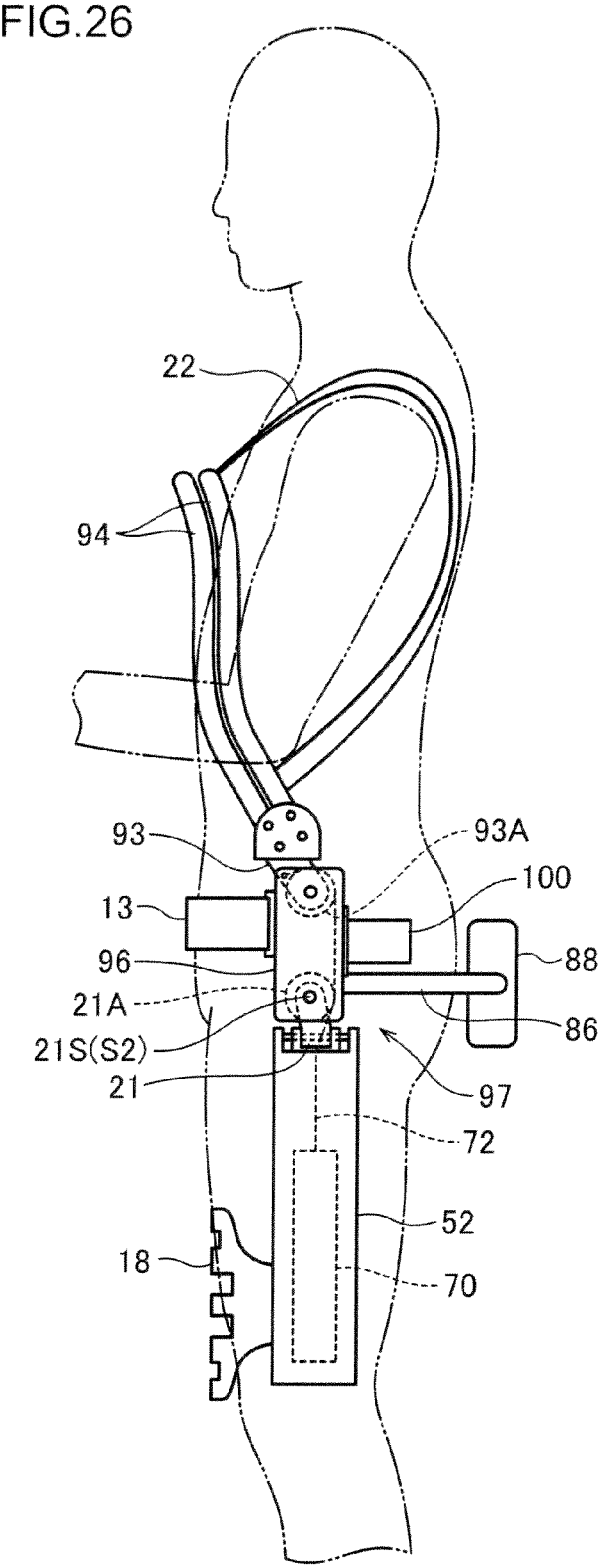
FIG. 26 is a side view illustrating a state of use of a lower back assistance apparatus according to a modified example of the third exemplary embodiment of the present invention.

In the present exemplary embodiment a back frame 94 mounted to the back of a user is employed as the upper body mounting section, however configuration may be made, as shown in FIG. 26, in which a chest frame 94F is employed for mounting to the chest of a user.

The two individual blocks 102K are also employed in the clutch sections 100 in the present exemplary embodiment, however a configuration can be made with a single block 102K. Another configuration can also be employed as a tension applying mechanism to the wires 72. For example, as shown in FIG. 27A, FIG. 27B and FIG. 27C, one end of each of the upper coupling frames 96 may be formed with an arm 110 that is rotatably supported by a shaft, a block 102K fixed to the arm 110 that has a saw-tooth profile on the end face, and a guide groove 112 formed in each of the upper coupling frames 96 along the path of the block 102K. A first and second end of each of the coil springs 105 is respectively anchored to the upper coupling frames 96 and the arm 110. The saw-tooth end face profiled arm 110 meshes with an arm 113 having a ratchet pawl, thereby connecting the arm 113 to an air cylinder 114. The purpose of such a structure is to enable free movement for the person to whom a lower back assistance apparatus is mounted, and also wires are taut when bending forward to lift up an object, and wires are slack when standing upright. The ratchet mechanism is released when air is injected into an air cylinder and the air cylinder actuated. enabling movement along the guide groove 112. such that a function is exhibited preventing the wires from becoming slack or becoming detached by a certain force being applied to each of the wires. Air is supplied into the actuators 40 on actuation to provide lower back assistance for a user lifting an object, and the actuators 40 contract so as to generate a force pulling the wires in a raising direction. Air is let out of the air cylinder 114 at the same time. Consequently, as shown in FIG. 27A and FIG. 27B, meshing of the arm 113 with ratchet pawl with the saw-toothed end face profile on the arm 110 is maintained irrespective of the positions of the wires and the blocks 102K. Biasing force towards the user forward direction Fr is applied with good efficiency due to the actuators 40 contracting with no slack.

Detailed explanation has been given of the present invention by way of particular specific exemplary embodiments, however the present invention is not limited by such exemplary embodiments and various other exemplary embodiments are possible within the scope of the present invention. For example, whereas in the present exemplary embodiment pneumatic actuators are employed as actuators, a wire wound onto or unwound from a rotating body by operating a motor may be employed as an actuator. A clutch rendering a rotating body non-rotatable or rotatable may also be employed as an actuator.

The invention claimed is:

1. A lower back assistance apparatus comprising:
an upper body mounting section for mounting to an upper body of a user and capable of following movement of a user tilting forward;
a support section attached to the upper body mounting section, extending towards a user trunk front side or trunk rear side, and supporting the user at the trunk front side or trunk rear side;
a lower limb mounting section for mounting to a lower limb of the user at least at a front side of the lower limb;
a coupling section, a portion at a first end of the coupling section being coupled to the lower limb mounting section, a portion at the second end of the coupling section being coupled by a first joint section so as to enable relative movement of the coupling section with respect to the upper body mounting section so as to permit the following movement of the upper body mounting section, and the coupling section being capable of maintaining a non-bent profile during the relative movement; and
an actuator that in an actuated state causes a force to act on the upper body mounting section countering the forward tilting of the user, wherein:
a wire extends out from a first end of the actuator;
a pretension application mechanism is provided at the first joint section, the pretension application mechanism is provided with a rotation body with a peripheral section around which the wire is wrapped, and the pretension application mechanism is in a relationship with the wire whereby the pretension application mechanism applies pretension to the wire such that tension force of the wire acts on the upper body mounting section or on the coupling section from the time of initial actuation of the actuator; and, a clutch mechanism is provided at the first joint section, the clutch mechanism is provided with a block section with a peripheral section around which the wire is wrapped, and the clutch mechanism is configured so as to press the block section toward the user forward direction against the wire when the actuator is actuated such that tension force of the wire acts on the upper body mounting section or on the coupling section from the time of initial actuation of the actuator, wherein the clutch mechanism is configured to cut off the relationship between the wire and the pretension application mechanism when the actuator operates to cause a force to act on the upper body mounting section in a user raising operation.

2. The lower back assistance apparatus of claim 1, wherein the first joint section is configured to enable relative rotation between the upper body mounting section and the coupling section about an axis running along a user left-right direction.

3. The lower back assistance apparatus of claim 2, wherein the coupling section further comprises a second joint section that is located further to a lower limb mounting section side than the first joint section, and the second joint section enables relative rotation between the lower limb mounting section and the coupling section about an axis running along the user left-right direction.

4. The lower back assistance apparatus of claim 1, wherein the upper body mounting section and the coupling section are coupled together about an axis running along a user front-rear direction such that the upper body mounting section and the coupling section are capable of relative rotation with respect to each other.

5. The lower back assistance apparatus of claim 1, further comprising a buttock mounting section coupled to the coupling section and adapted to be mounted to the buttocks of the user.

6. The lower back assistance apparatus of claim 1, wherein the actuator is a pneumatic actuator that contracts when internally supplied with air.

7. The lower back assistance apparatus of claim 1, wherein the actuator is disposed at the lower body mounting section.

* * * * *